US012668770B2

(12) United States Patent
Wada et al.

(10) Patent No.: US 12,668,770 B2
(45) Date of Patent: Jun. 30, 2026

(54) METHOD OF IMPROVING RESISTANCE TO SUBSTRATE ANALOG OF NITRIC ACID IN MICROALGA

(71) Applicant: Kao Corporation, Tokyo (JP)

(72) Inventors: Mayumi Wada, Wakayama (JP);
Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 811 days.

(21) Appl. No.: 16/499,945

(22) PCT Filed: Apr. 2, 2018

(86) PCT No.: PCT/JP2018/014097

§ 371 (c)(1),
(2) Date: Oct. 1, 2019

(87) PCT Pub. No.: WO2018/190170

PCT Pub. Date: Oct. 18, 2018

(65) Prior Publication Data

US 2021/0102161 A1      Apr. 8, 2021

(30) Foreign Application Priority Data

Apr. 12, 2017      (JP) ................................. 2017-078886

(51) Int. Cl.
*C12N 1/12*            (2026.01)

(52) U.S. Cl.
CPC ...................................... *C12N 1/12* (2013.01)

(58) Field of Classification Search
CPC ...................................................... C12N 1/12
See application file for complete search history.

(56) References Cited

FOREIGN PATENT DOCUMENTS

WO      WO 2009/009142 A2      1/2009
WO      WO 2009/095455 A1      8/2009

OTHER PUBLICATIONS

Kilian et al. "High-efficiency homologous recombination in the oil-producing alga *Nannochloropsis sp.*", Proceedings of the National Academy of Sciences of the United States of America, 2011, vol. 108, No. 52, pp. 21265-21269. (Year: 2011).*
Solomonson et al. "Nitrate reductase and chlorate toxicity in Chlorella vulgaris Beijerinck", Plant Physiology, 1972, vol. 50, Issue 4, pp. 421-424. (Year: 1972).*

Wang et al. "Genome editing of model oleaginous microalgae *Nannochloropsis spp.* by CRISPR/Cas9", The Plant Journal, 2016, vol. 88, Issue 6, pp. 1071-1081 (Year: 2016).*
Andersen et al. "Phylogeny of the Eustigmatophysceae based upon 18S rDNA, with Emphasis on Nannochloropsis", Protist, 1998, vol. 149, Issue 1, pp. 61-74. (Year: 1998).*
International Search Report (ISR) for PCT/JP2018/014097; I.A. fd Apr. 2, 2018, mailed Jun. 26, 2018 from the Japan Patent Office, Tokyo, Japan.
International Preliminary Report on Patentability (IPRP), Chapter I of the Patent Cooperation Treaty, including the Written Opinion for PCT/JP2018/014097; I.A. fd Apr. 2, 2018, issued Oct. 15, 2019, by the International Bureau of WIPO, Geneva, Switzerland.
Kilian, O et al., "High-efficiency homologous recombination in the oil-producing alga *Nannochloropsis sp.*," Proc Natl Acad Sci U S A. Dec. 27, 2011;108(52):21265-9. doi: 10.1073/pnas.1105861108. Epub Nov. 28, 2011.
Nelson, J.A.E. et al., "Targeted disruption of the NIT8 gene in *Chlamydomonas reinhardtii*," Mol Cell Biol. Oct. 1995; 15(10):5762-9.
Author unknown: Strain Data: NIES-2145, downloaded Dec. 5, 2023 from https://mcc.nies.go.jp/numberSearch.do.
Author unknown: MailNews MCC (Microbial Culture Collection) No. 4 (Jan. 13, 2017) https://mcc.nies.go.jp/mcc_mail_news/mailnewsNo4.pdf.
Yang HP, Wenzel M, Hauser DA, Nelson JM, Xu X, Eliáš M, Li FW. Monodopsis and Vischeria Genomes Shed New Light on the Biology of Eustigmatophyte Algae. Genome Biol Evol. Nov. 5, 2021;13(11):evab233. doi: 10.1093/gbe/evab233.
Wu D, et al., Transcriptome analysis of lipid metabolism in response to cerium stress in the oleaginous microalga Nannochloropsis oculata. Sci Total Environ. Sep. 10, 2022;838(Pt 3):156420. doi: 10.1016/j.scitotenv.2022.156420. Epub Jun. 1, 2022.
Supplemental material to Wu D, et al., Transcriptome analysis of lipid metabolism in response to cerium stress in the oleaginous microalga Nannochloropsis oculata. Sci Total Environ. Sep. 10, 2022;838(Pt 3):156420. doi: 10.1016/j.scitotenv.2022.156420. Epub Jun. 1, 2022.

* cited by examiner

*Primary Examiner* — Louise W Humphrey
*Assistant Examiner* — Deepa Mishra
(74) *Attorney, Agent, or Firm* — Element IP, PLC

(57) ABSTRACT

Provided is a method of improving resistance to a substrate analog of nitric acid in a microalga, comprising deleting a gene encoding the following protein (A) or (B) present in the genome of the microalga, or downregulating expression of a gene encoding the following protein (A) or (B): wherein protein (A) is a protein consisting of the amino acid sequence set forth in SEQ ID NO:41; and wherein protein (B) is a protein consisting of an amino acid sequence having 70% or more identity with the amino acid sequence of protein (A), and having nitrate transporter activity.

13 Claims, 5 Drawing Sheets

Specification includes a Sequence Listing.

Pvcp1-ble-Tvcp1: fragment of cassette for zeocin resistance gene expression

FIG. 4A
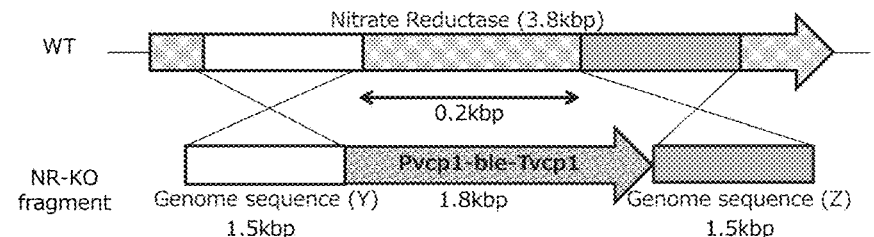
WT
NR-KO fragment
FIG. 4B
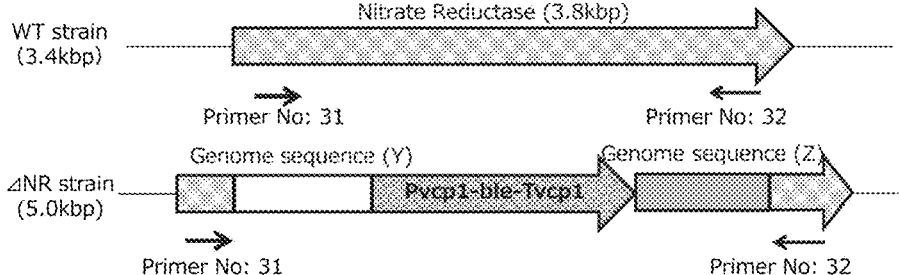
FIG. 4C

FIG. 6A

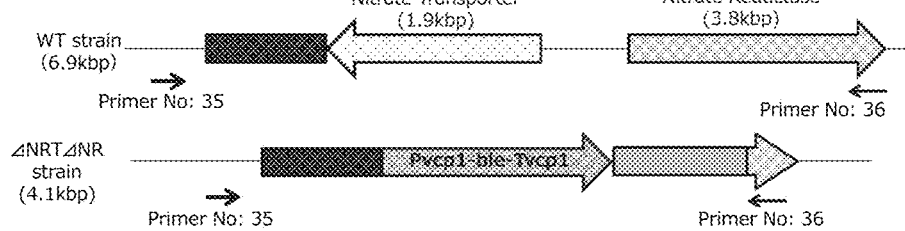

WT 1.6kbp        Nitrate Transporter (1.9kbp)        0.9kbp        1.8kbp        1.5kbp Nitrate Reductase (3.8kbp)

NRT-NR-KO fragment (1)

Genome sequence (W) 1.6kbp        Pvcp1-ble-Tvcp1        1.8kbp        Genome sequence (Z) 1.5kbp

FIG. 6B

WT strain (6.9kbp)

Nitrate Transporter (1.9kbp)        Nitrate Reductase (3.8kbp)

Primer No: 35        Primer No: 36

ΔNRTΔNR strain (4.1kbp)

Pvcp1-ble-Tvcp1

Primer No: 35        Primer No: 36

FIG. 6C

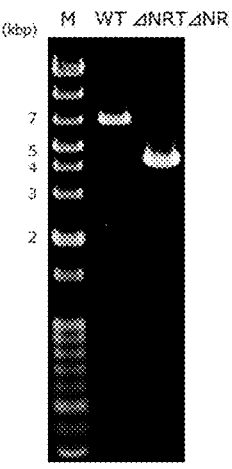

(kbp)    M    WT  ΔNRTΔNR 7
5
4
3
2

FIG. 7

|  | WT strain | ΔNR strain | ΔNTR strain | ΔNTRΔNR strain |
|---|---|---|---|---|
| Nitrate agar media |  |  |  |  |
| Urea agar media |  |  |  |  |
| Urea agar media containing 5mM KClO₃ |  |  |  |  |

METHOD OF IMPROVING RESISTANCE TO SUBSTRATE ANALOG OF NITRIC ACID IN MICROALGA

TECHNICAL FIELD

The present invention relates to a method of improving resistance to a substrate analog of nitric acid in a microalga, a transformant of a microalga having resistance to a substrate analog of nitric acid, and a method of preparing a transformant having resistance to a substrate analog of nitric acid.

BACKGROUND ART

Culture of microorganisms for producing a biofuel or other useful substance is generally performed on the assumption of culturing pure culture of target microorganisms. Accordingly, in order to prevent contamination by microorganisms other than the desired microorganisms, sterilization treatment or germicidal treatment is usually applied to the culture medium or incubator.

However, as scale of microorganism cultivation is expanded, the cost of energy and equipment required for the sterilization or germicidal treatment of the culture medium and the like increases. Further, even if culture medium subjected to sterilization or germicidal treatment is used, growth of non-targeted microorganisms owing to contamination arising after the treatment is hard to avoid. When microorganisms (typically microalgae) are cultured in an open area using an open-type open pond or the like, risk of contamination is particularly high.

Therefore, an urgent need is felt for the development of a method of culturing microbial strains or microorganisms that can inhibit growth of non-targeted microorganisms and selectively culture target microorganisms over a long period of time.

One method of preventing microbial contamination is to use microorganisms into which a foreign gene marker such as an antibiotic-resistant gene is introduced by a gene recombination technology. However, a strain prepared by introducing a foreign gene corresponds to a gene recombinant, and use thereof is restricted under the regulatory requirements of the Cartagena Protocol, for example, owing to its risk of spreading the foreign gene across the natural environment. For example, the possibility of the foreign gene introduced into a cell of the microorganism spreading to other species by horizontal transfer or similar is a concern.

Attention is therefore being focused on technologies for selectively culturing target microorganisms not by using a foreign gene but by modifying an endogenous gene and utilizing the properties obtained.

A gene encoding nitrate reductase (hereinafter, also referred to as "NR") (hereinafter, also referred to as "NR gene") exists as an endogenous gene (see Non-Patent Literature 1). NR is a kind of a nitrogen metabolizing enzyme that catalyzes reduction reaction of nitrate ion ($NO_3^-$) to nitrite ion ($NO_2^-$), as shown in FIG. 1. Moreover, NR can also catalyze reduction reaction of chlorate ion ($ClO_3^-$), which is a substrate analog of nitrate ion, to chlorite ion ($ClO_2^-$). It is generally known that chlorite ion exhibits cytotoxicity and that expression of the NR gene is down-regulated, whereby the microorganisms can be grown even in the presence of chloric acid. So it should be possible to utilize chloric acid resistance enhanced by NR gene inhibition to selectively cultivate target microorganisms.

Moreover, a nitrate transporter (hereinafter, also referred to as "NRT") exists as a protein associated with nitrogen assimilation. The NRT is a protein that transports nitrate ion from an external source into the cell at initial stage of nitrogen assimilation (nitrate assimilation) in organisms. It is reported that the resistance to chloric acid can be provided by downregulating expression of a gene encoding the NRT (hereinafter, also merely referred to as "NRT gene") in *Chlamydomonas reinhardtii* (see Non-Patent Literature 2).

In recent years, microalgae attract attention due to its usefulness in biofuel production. Especially, the microalgae of the class Eustigmatophyceae, such as microalgae belonging to the genus *Nannochloropsis*, can produce lipids that can be used as the biodiesel fuels and the food materials through photosynthesis. Further, the microalgae attract attention as next-generation biomass resources, because the microalgae do not compete with foods.

Therefore, in order to realize a countermeasure against contamination when these microalgae are cultured outdoors using an open pond or the like, it is desirable to develop a method, employing some kind of drug-resistance indicator, that cultures target algae using endogenous genes with no use of foreign genes. However, nothing has been reported regarding use of endogenous gene of microalgae in the class Eustigmatophyceae to impart drug resistance.

CITATION LIST

Non-Patent Literatures

Non-Patent Literature 1: Proceedings of the National Academy of Sciences, 2011, vol. 108 (52), p. 21265-21269

Non-Patent Literature 2: Mol. Cell. Biology, 1995, vol. 15 (10), p. 5762-5769

SUMMARY OF INVENTION

The present invention relates to a method of improving resistance to a substrate analog of nitric acid in a microalga, containing deleting a gene encoding the following protein (A) or (B) present in the genome of the microalga, or downregulating expression of a gene encoding the following protein (A) or (B).

Further, the present invention relates to a method of improving resistance to a substrate analog of nitric acid in a microalga, containing deleting a gene or downregulating gene expression for each a gene encoding the following protein (A) or (B) and a gene encoding the following protein (C) or (D) present in the genome of the microalga.

{0008}

(A) a protein consisting of the amino acid sequence set forth in SEQ ID NO: 41, (B) a protein consisting of an amino acid sequence having 70% or more identity with the amino acid sequence of the protein (A), and having nitrate transporter activity (hereinafter, also merely referred to as "NRT activity"), (C) a protein consisting of the amino acid sequence set forth in SEQ ID NO: 42, and (D) a protein consisting of an amino acid sequence having 70% or more identity with the amino acid sequence of the protein (C), and having nitrate reductase activity (hereinafter, also merely referred to as "NR activity").

{0009}

Further, the present invention relates to a transformant of a microalga having resistance to a substrate analog of nitric acid, wherein a gene encoding the protein (A) or (B) present in the genome is deleted, or expression of a gene encoding the protein (A) or (B) is downregulated.

Further, the present invention relates to a transformant of a microalga having resistance to a substrate analog of nitric acid, wherein a gene is deleted or gene expression is downregulated for each a gene encoding the protein (A) or (B) and a gene encoding the protein (C) or (D) present in the genome.

{0010}

Further, the present invention relates to a method of preparing a transformant having resistance to a substrate analog of nitric acid by deleting a gene encoding the protein (A) or (B) present in the genome of a microalga, or downregulating expression of a gene encoding the protein (A) or (B), thereby obtaining the transformant using resistance to the substrate analog of nitric acid as an indicator.

Furthermore the present invention relates to a method of preparing a transformant having resistance to a substrate analog of nitric acid by deleting a gene or downregulating gene expression for each a gene encoding the protein (A) or (B) and a gene encoding the protein (C) or (D) present in the genome of a microalga, thereby obtaining the transformant using resistance to the substrate analog of nitric acid as an indicator.

Other and further objects, features and advantages of the invention will appear more fully from the following description, appropriately referring to the accompanying drawings.

BRIEF DESCRIPTION OF DRAWINGS

{0011}

Figure 1:
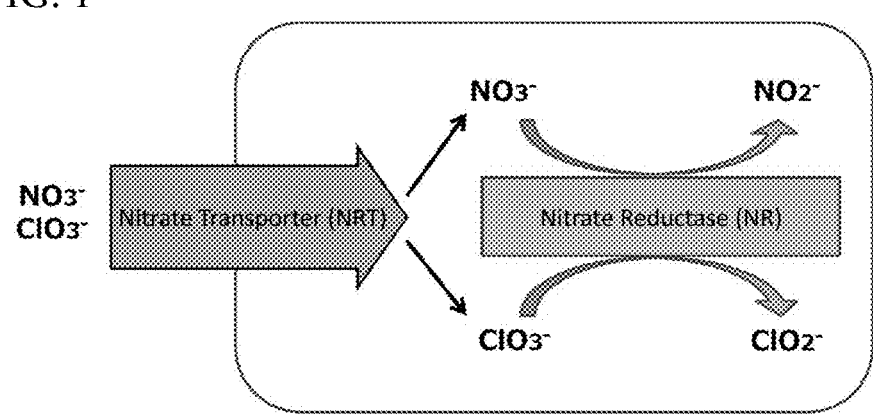

FIG. 1 is a diagram schematically showing a metabolic pathway of nitrate ion and its substrate analog (chlorate ion), which is performed in association of an NR with an NRT in a microalga.

Figure 2:
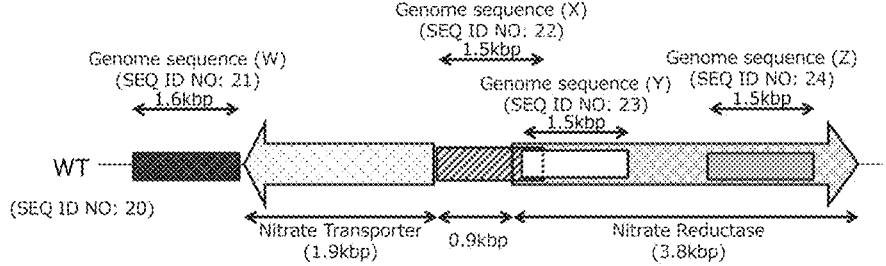

FIG. 2 is a diagram schematically showing a genome sequence around an NRT gene and an NR gene in a wild-type strain of *Nannochloropsis oculata.*

Figure 3A:
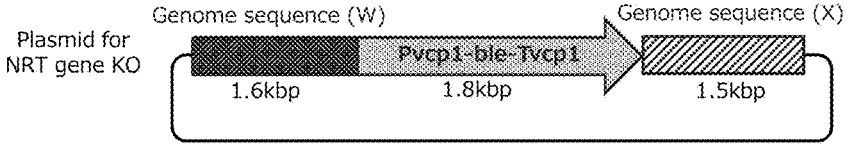
Figure 3B:
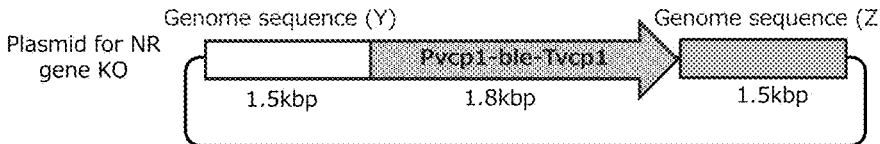
Figure 3C:
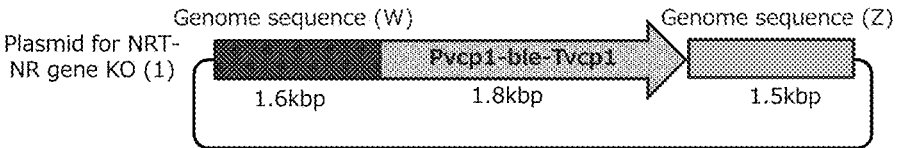

FIG. 3A is a schematic diagram of a plasmid for homologous recombination of the NRT gene prepared in Example 1. FIG. 3B is a schematic diagram of plasmid for homologous recombination of the NR gene prepared in Example 1. FIG. 3C is a schematic diagram of a plasmid for homologous recombination of the NRT-NR gene prepared in Example 1.

FIG. 4A is a diagram schematically showing a method of preparing an NR gene-disrupted strain using a cassette for homologous recombination of the NR gene. FIG. 4B is a schematic diagram for comparing sizes of DNA fragments to be amplified for confirming introduction of a cassette by homologous recombination between a wild-type strain of *Nannochloropsis oculata* and the NR gene-disrupted strain. FIG. 4C is an electrophoresis photograph (photograph substituted for drawing) of genome fragments amplified by PCR.

Figure 5A:
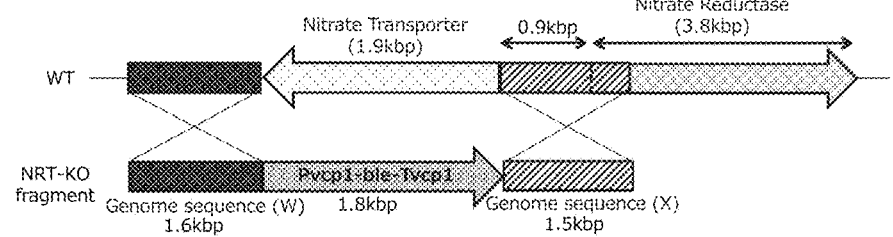
Figure 5B:
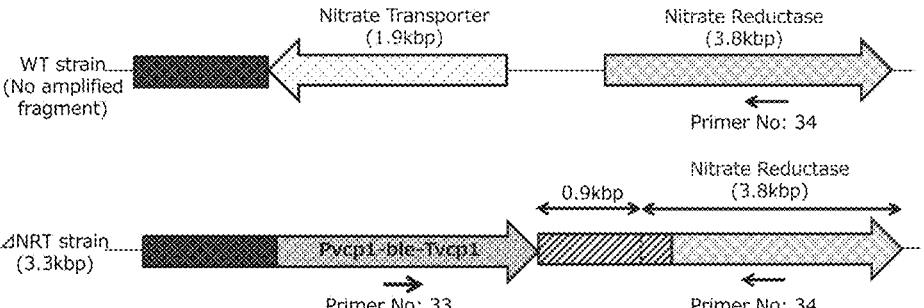
Figure 5C:
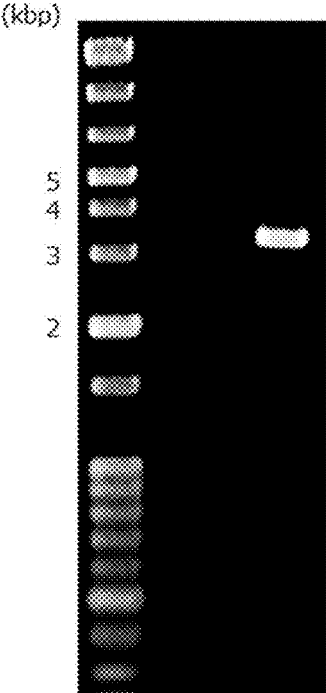

FIG. 5A is a diagram schematically showing a method of preparing an NRT gene-disrupted strain using a cassette for homologous recombination of the NRT gene. FIG. 5B is a schematic diagram for comparing sizes of DNA fragments to be amplified for confirming introduction of a cassette by homologous recombination between a wild-type strain of *Nannochloropsis oculata* and the NRT gene-disrupted strain. FIG. 5C is an electrophoresis photograph (photograph substituted for drawing) of genome fragments amplified by PCR.

FIG. 6A is a diagram schematically showing a method of preparing an NRT-NR gene-disrupted strain using a cassette for homologous recombination of the NRT-NR gene. FIG. 6B is a schematic diagram for comparing sizes of DNA fragments to be amplified for confirming introduction of a cassette by homologous recombination between a wild-type strain of *Nannochloropsis oculata* and the NRT-NR gene-disrupted strain. FIG. 6C is an electrophoresis photograph (photograph substituted for drawing) of genome fragments amplified by PCR.

FIG. 7 is a photograph substituted for drawing wherein each transformant prepared in Example 1 was cultured in agar media.

Figure 8A:
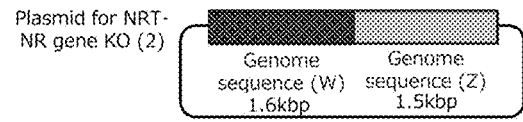
Figure 8B:
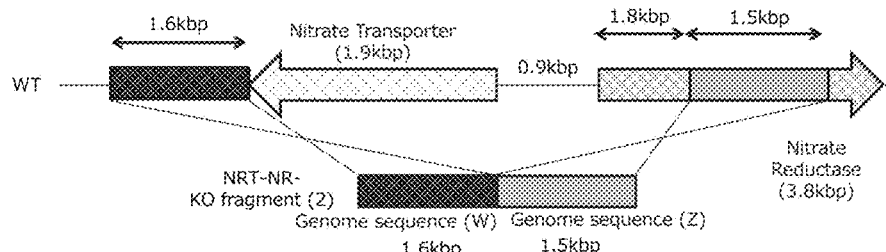
Figure 8C:
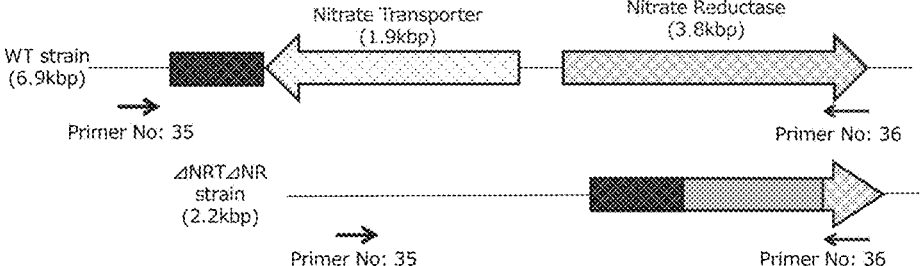
Figure 8D:
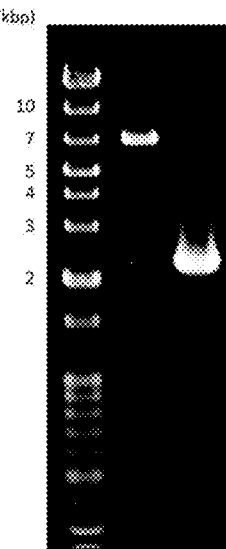

FIG. 8A is a schematic diagram of a plasmid for homologous recombination of the NRT-NR gene prepared in Example 2. FIG. 8B is a diagram schematically showing a method of preparing an NRT gene and NR gene-disrupted strain using a cassette for homologous recombination of the NRT gene and the NR gene. FIG. 8C is a schematic diagram for comparing sizes of DNA fragments to be amplified for confirming introduction of a cassette by homologous recombination between a wild-type strain of *Nannochloropsis oculata* and the NRT gene and the NR gene-disrupted strain. FIG. 8D is an electrophoresis photograph (photograph substituted for drawing) of genome fragments amplified by PCR.

DESCRIPTION OF EMBODIMENTS

{0012}

As stated above, substantially nothing has been reported in a microalga in class Eustigmatophyceae regarding a method of preparing a microalga improving drug-resistance by modifying an endogenous gene without using a foreign gene.

Therefore, the present invention is directed to provision of an alga capable of selective pure culture over a long period of time by modifying an endogenous gene without using a foreign drug gene marker.

{0013}

The present inventors diligently studied in view of the above-described problems.

The present inventors first exploited the prior art described in Non-Patent Literature 1 to obtain a strain in which an NR gene of *Nannochloropsis* in the class Eustigmatophyceae was disrupted to inhibit expression of the gene and thereafter confirmed resistance to chloric acid, which is a substrate analog of nitric acid. However, no improvement in chloric acid resistance as generally reported was observed.

Further, the present inventors attempted downregulation of NRT gene expression in accordance with the disclosure regarding *Chlamydomonas reinhardtii* set out in Non-Patent Literature 2. However, the NRT gene of *Nannochloropsis* has not been identified so far.

{0014}

Therefore, the present inventors newly identified the NRT gene of *Nannochloropsis*, and disrupted the identified NRT gene to measure the chloric acid resistance of the obtained transformant. As a result, the chloric acid resistance was improved, as compared with the case where only the NR gene was disrupted.

Further, the present inventors prepared a transformant in which the NRT gene and the NR gene were disrupted to measure the chloric acid resistance. As a result, the present inventors also found that the chloric acid resistance is significantly improved by suppression of both the NRT and the NR activities.

Then, the present inventors found that the transformant is cultured in the presence of the substrate analog of nitric acid, such as chloric acid, whereby growth of non-targeted microorganisms can be suppressed, and the above-described transformant can be selectively cultured.

The present invention has been achieved on the basis of these findings.

{0015}

According to the method of improving resistance to the substrate analog of nitric acid in the microalga of the present invention, the resistance to the substrate analog of nitric acid in the microalga can be improved to such an extent that selective pure culture for a long period of time can be achieved without introducing a foreign gene.

Moreover, since the transformant of the present invention is excellent in resistance to the substrate analog of nitric acid, the transformant can be cultured for a long period of time even under selective pressure conditions (under conditions of the substrate analog of nitric acid).

Further, according to the method of preparing the transformant of the present invention, the transformant capable of long-term culturing even under the selective pressure conditions (under the conditions of the substrate analog of nitric acid) without introducing a foreign gene can be prepared using resistance to the substrate analog of nitric acid as an indicator.

{0016}

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in the present specification, the "stringent conditions" includes, for example, the method described in Molecular Cloning-A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a site of 5' end side or a region subsequent to 5' end side of a targeted gene or region, and not a position from a translational initiation site. On the other hand, the term "downstream" of the gene means a site of 3' end side or a region subsequent to 3' end side of the targeted gene or region.

Moreover, in the present specification, the microalga obtained by modifying a desired gene of a host is referred to as the "transformant".

{0017}

In the first embodiment of the present invention, an NRT gene on the genome of a specific microalga is deleted. Alternatively, expression of the NRT gene encoded in the genome of the specific microalga is downregulated. The NRT gene described later is deleted or expression thereof is downregulated in the specific microalga, whereby resistance to the substrate analog of nitric acid, preferably chloric acid resistance, influencing viability of the microalga, is improved. The transformant of the present invention can also be selected using improved resistance to the substrate analog of nitric acid (preferably chloric acid resistance) as an indicator.

Further, as mentioned above, a chlorite ion formed by reduction of a chlorate ion by nitrogen metabolism exhibits high toxicity to ordinary microorganisms. However, the transformant of the present invention has high resistance to chloric acid. Therefore, when the transformant of the present invention is cultured in a chloric acid-containing medium, contamination by non-targeted microorganisms can be prevented. In particular, even if the transformant of the present invention is cultured in an open area with high susceptibility to invasion of various microorganisms and their nutrient sources, sufficient and appropriate measures can be implemented against contamination during culture.

As termed in the present specification "NRT gene" means not only gene including DNA formed of the nucleotide sequence in the region encoding NRT but also DNA formed of the nucleotide sequence in the region adjusting expression of the NRT and DNA formed of the nucleotide sequences in the region encoding the NRT and the region adjusting expression of the NRT.

{0018}

The NRT of the present invention indicates the protein (A) or (B). The amino acid sequence set forth in SEQ ID NO: 41 is an NRT derived from *Nannochloropsis oculata* strain NIES-2145 (hereinafter, also referred to as "NONRT"). In addition, identity of the amino acid sequence set forth in SEQ ID NO: 41 to the amino acid sequence of the NRT of *Chlamydomonas reinhardtii* (described in Non-Patent Literature 2) is around 38%.

Both of the proteins (A) and (B) have NRT activity. In the present specification, the term "NRT activity" means transport ability of nitrate ion or chlorate ion from an external source into the cells.

{0019}

The protein having the NRT activity can be confirmed, for example, by introducing DNA linked with the gene encoding the above-described protein in the downstream of a promoter which functions in a host cell into the host cell in which a transporter of nitrate ion is deficient to culture the cell under the conditions in which the thus introduced gene is expressed, thereby analyzing whether or not the cell can grow by using nitric acid as a nitrogen source.

{0020}

The protein (B) consists of an amino acid sequence having 70% or more identity with the amino acid sequence of the protein (A), and has the NRT activity.

In general, it is known that an amino acid sequence encoding a protein does not necessarily exhibit function as the protein unless the sequence in the whole region is conserved, and there exists a region in which the function is not influenced even if the amino acid sequence is changed. In such a region which is not essential to the function, even if the mutation of the amino acid, such as deletion, substitution, insertion and addition thereof is introduced thereinto, the function inherent to the protein can be maintained. Also in the present invention, such a protein can be used in which the NRT activity is kept and a part of the amino acid sequence is subjected to mutation.

{0021}

In the protein (B), the identity with the amino acid sequence of the protein (A) is preferably 75% or more, more preferably 80% or more, further preferably 85% or more, further preferably 90% or more, further preferably 92% or more, further preferably 95% or more, further preferably 98% or more, and furthermore preferably 99% or more, in view of the NRT activity. Further, specific examples of the protein (B) include a protein in which 1 or several (for example 1 or more and 141 or less, preferably 1 or more and 117 or less, more preferably 1 or more and 94 or less, further preferably 1 or more and 71 or less, furthermore preferably 1 or more and 47 or less, furthermore preferably 1 or more and 38 or less, furthermore preferably 1 or more and 24 or less, furthermore preferably 1 or more and 10 or less, and furthermore preferably 1 or more and 5 or less) amino acids are deleted, substituted, inserted or added to the amino acid sequence of the protein (A).

{0022}

An example of a gene encoding the protein (A) or (B) includes a gene consisting of the following DNA (a) or (b).

(a) a DNA consisting of the nucleotide sequence set forth in SEQ ID NO: 39; and (b) a DNA consisting of a nucleotide sequence having 55% or more identity with the nucleotide sequence of the DNA (a), and encoding a protein having the NRT activity;

The nucleotide sequence set forth in SEQ ID NO: 39 is a nucleotide sequence of a gene encoding the NONRT.

{0023}

In the DNA (b), the identity with the nucleotide sequence of the DNA (a) is preferably 60% or more, more preferably 65% or more, further preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of the NRT activity. Further, the DNA (b) is also preferably a DNA in which 1 or several (for example 1 or more and 634 or less, preferably 1 or more and 563 or less, more preferably 1 or more and 493 or less, further preferably 1 or more and 423 or less, further preferably 1 or more and 352 or less, further preferably 1 or more and 282 or less, further preferably 1 or more and 212 or less, further preferably 1 or more and 141 or less, further preferably 1 or more and 113 or less, further preferably 1 or more and 71 or less, further preferably 1 or more and 29 or less, and furthermore preferably 1 or more and 15 or less) nucleotides are deleted, substituted, inserted or added to the nucleotide sequence of the DNA (a), and encoding the protein (A) or (B) having the NRT activity. Furthermore, the DNA (b) is also preferably a DNA capable of hybridizing with a DNA consisting of the nucleotide sequence complementary with the DNA (a) under a stringent condition, and encoding the protein (A) or (B) having the NRT activity.

{0024}

The NRT gene can be obtained by genetic engineering techniques that are ordinarily carried out. For example, the NRT gene can be artificially synthesized based on the amino acid sequence set forth in SEQ ID NO: 41, or the nucleotide sequence set forth in SEQ ID NO: 39. The synthesis of the NRT gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. *Nannochloropsis oculata* NIES-2145 used in Examples can be obtained from National Institute for Environmental Studies (NIES).

{0025}

In the second embodiment of the present invention, in addition to the above-mentioned NRT gene, the NR gene is also deleted or expression thereof is downregulated. These genes are deleted or expression thereof is downregulated, whereby the resistance to the substrate analog of nitric acid is further improved. Therefore, the obtained transformant can grow even under conditions containing the substrate analog of nitric acid, preferably chloric acid with a higher concentration. Accordingly, the transformant of the present invention can be selected using the resistance to the substrate analog of nitric acid (preferably chloric acid resistance) as the indicator. Here, the term "NR" herein means an enzyme which reduces nitrate ion to form nitrite ion. Moreover, the NR reduces chlorate ion as the substrate analog of nitrate ion to form chlorite ion As termed in the present specification "NR gene" means not only gene including DNA formed of the nucleotide sequence in the region encoding NR but also DNA formed of the nucleotide sequence in the region adjusting expression of the NR and DNA formed of the nucleotide sequences in the region encoding the NR and the region adjusting expression of the NR.

In addition, in the present specification, the expression: the NRT gene and the NR gene "are deleted or expression thereof is downregulated" means gene manipulation indicated in the following (I), (II), (III) or (IV).

(I) Deleting the NRT gene and the NR gene, respectively.

(II) Suppressing expression of the NRT gene and the NR gene, respectively.

(III) Deleting the NRT gene, and downregulating expression of the NR gene.

(IV) Suppressing expression of the NRT gene, and deleting the NR gene.

{0026}

The NR of the present invention indicates the protein (C) or (D). A protein consisting of the amino acid sequence of SEQ ID NO: 42 is an NR derived from *Nannochloropsis oculata* strain NIES-2145 (hereinafter, also referred to as "NoNR").

Both of the protein (C) and (D) have the NR activity. In the present specification, the term "NR activity" means activity which catalyzes the reduction reaction of nitrate ion to form nitrite ion, or activity which catalyzes the reduction reaction of chlorate ion to form chlorite ion.

{0027}

The protein (D) consists of an amino acid sequence having 70% or more identity with the amino acid sequence of the protein (C), and has the NR activity.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the NR activity is kept and a part of the amino acid sequence is subjected to mutation.

{0028}

In the protein (D), the identity with the amino acid sequence of the protein (C) is preferably 75% or more, more preferably 80% or more, further preferably 85% or more, further preferably 90% or more, further preferably 92% or more, further preferably 95% or more, further preferably 98% or more, and furthermore preferably 99% or more, in view of the NR activity. Further, specific examples of the protein (D) include a protein in which 1 or several (for example 1 or more and 255 or less, preferably 1 or more and 212 or less, more preferably 1 or more and 170 or less, further preferably 1 or more and 128 or less, furthermore preferably 1 or more and 85 or less, furthermore preferably 1 or more and 68 or less, furthermore preferably 1 or more and 43 or less, furthermore preferably 1 or more and 17 or less, and furthermore preferably 1 or more and 9 or less) amino acids are deleted, substituted, inserted or added to the amino acid sequence of the protein (C).

{0029}

Note that the algae such as *Nannochloropsis oculata* can be obtained from culture collection such as private or public research institutes or the like. For example, *Nannochloropsis oculata* strain NIES-2145 can be obtained from National Institute for Environmental Studies (NIES).

{0030}

An example of a gene encoding the NR, preferably the protein (C) or (D), includes a gene consisting of the following DNA (c) or (d).

(c) a DNA consisting of the nucleotide sequence set forth in SEQ ID NO: 40; and (d) a DNA consisting of a nucleotide sequence having 70% or more identity with the nucleotide sequence of the DNA (c), and encoding a protein having the NR activity.

The nucleotide sequence set forth in SEQ ID NO: 40 is a nucleotide sequence of a gene encoding the NoNR.

{0031}

In the DNA (d), the identity with the nucleotide sequence of the DNA (c) is preferably 75% or more, more preferably 80% or more, further preferably 85% or more, further preferably 90% or more, further preferably 92% or more, further preferably 95% or more, further preferably 98% or more, and furthermore preferably 99% or more, in view of the NR activity. Further, the DNA (d) is also preferably a DNA in which 1 or several (for example 1 or more and 764 or less, preferably 1 or more and 636 or less, more preferably 1 or more and 509 or less, further preferably 1 or more and 382 or less, further preferably 1 or more and 255 or less, further preferably 1 or more and 204 or less, further preferably 1 or more and 128 or less, further preferably 1 or more and 51 or less, and furthermore preferably 1 or more and 26 or less) nucleotides are deleted, substituted, inserted or added to the nucleotide sequence set forth in SEQ ID NO: 40, and encoding the protein (C) or (D) having the NR activity. Furthermore, the DNA (d) is also preferably a DNA capable of hybridizing with a DNA consisting of the nucleotide sequence complementary with the DNA (c) under a stringent condition, and encoding the protein (C) or (D) having the NR activity.

{0032}

The NR gene can be obtained by genetic engineering techniques that are ordinarily carried out. For example, the NR gene can be artificially synthesized based on the amino acid sequence set forth in SEQ ID NO: 42, or the nucleotide sequence set forth in SEQ ID NO: 40. The synthesis of the NR gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. *Nannochloropsis oculata* NIES-2145 used in Examples can be obtained from National Institute for Environmental Studies (NIES).

In the present invention, a method of deleting the NRT gene or the NR gene present in the genome or downregulating expression thereof is not particularly limited, and can be appropriately selected from ordinary methods. The deletion of the NRT gene or the NR gene or the downregulation of expression thereof can be confirmed by analyzing genome sequence of the transformant, or by measuring the NRT activity or the NR activity according to an ordinary method.

For example, the NRT gene or the NR gene can be deleted by disrupting the NRT gene or the NR gene present in the genome. Specifically, appropriate DNA fragment containing a part of the NRT gene or the NR gene is incorporated into cells of the microalgae, and the whole or partial NRT gene or NR gene is replaced with other arbitrary DNA fragment (for example, an arbitrary selection marker) by homologous recombination in a partial region of the NRT gene or the NR gene, or the NRT gene or the NR gene is splitted by inserting arbitrary DNA fragment (for example, an arbitrary selection marker), whereby the NRT gene or the NR gene can be deleted.

Moreover, methods of downregulating expression of genes at random include a method of inducing mutation of the NRT gene or the NR gene by use of a mutagen such as N-methyl-N'-nitro-N-nitrosoguanidine, or irradiation with ultraviolet light, gamma rays or the like, a method of inducing site-specific point mutation (for example, frame-shift mutation, in-frame mutation, insertion of a termination codon, or the like) into the NRT gene or the NR gene (for example, active site, substrate binding site, and transcription or translation initiation region), antisense method, RNA interference method, promoter competition, or the like.

In the present invention, the NRT gene or the NR gene in the genome is preferably deleted by disruption.

{0034}

A size of the DNA cassette for homologous recombination used for disruption of the NRT gene or the NR gene can be appropriately set in consideration of introduction efficiency into the microalgae, homologous recombination efficiency, a size of the several genes, and the like. For example, the size of the DNA cassette is preferably 400 bp or more, and more preferably 500 bp or more. Moreover, an upper limit thereof is preferably 2.0 kbp, and more preferably 2.5 kbp.

Further, genome length disrupted by homologous recombination is preferably 15 kbp or less, and more preferably 10 kbp or less. Further, the length of each of the genes incorporated thereinto is preferably 10 kbp or less, and more preferably 8 kbp or less.

{0035}

A transformation method for introducing the DNA cassette for homologous recombination into the microalgae can be appropriately selected from ordinary methods according to a kind of the microalgae.

Examples of the method for transformation include a transformation method of using calcium ion, a general competent cell transformation method, a protoplast transformation method, an electroporation method, an LP transformation method, a method of using *Agrobacterium*, a particle gun method, and the like. In addition, transformation can also be performed in the present invention by using the electroporation method described in Randor Radakovits, et al., Nature Communications, DOI: 10.1038/ncomms1688, 2012, or the like.

{0036}

The microalga used in the present invention is preferably a microalga of the class Eustigmatophyceae, more preferably a microalga of the order Eustigmatales, further preferably a microalga of the genus *Nannochloropsis*, from a viewpoint of establishing gene modification technology. Specific examples of the microalgae of the genus *Nannochloropsis* include *Nannochloropsis oculata*, *Nannochloropsis oceanica*, *Nannochloropsis gaditana*, *Nannochloropsis salina*, *Nannochloropsis atomus*, *Nannochloropsis maculata*, *Nannochloropsis granulata*, and *Nannochloropsis* sp. Among these, *Nannochloropsis oculata*, *Nannochloropsis oceanica* or *Nannochloropsis* gaditana is preferred, and *Nannochloropsis oculata* is more preferred.

{0037}

Selection of a transformant wherein the NRT gene or the NR gene is deleted or expression thereof is downregulated, is carried out according to an ordinary method. However, the selection is preferably carried out by using an indicator of resistance to a substrate analog of nitric acid, and more preferably carried out by using an indicator of chloric acid resistance.

Specifically, a viable strain when a concentration of the substrate analog of nitric acid (preferably chloric acid) or a salt thereof contained in the culture medium, and culturing period of the transformant are appropriately selected according to a kind of host, and the transformant is cultured in the presence of the substrate analog of nitric acid (preferably chloric acid) is selected as the transformant acquiring the resistance to the substrate analog of nitric acid (preferably chloric acid).

Concentration of chloric acid or a salt thereof contained in the culture medium is preferably 3 mM or more, and more preferably 5 mM or more. The culturing period is preferably one (1) week or more, and more preferably two (2) weeks or more, and preferably eight (8) weeks or less.

{0038}

In the transformant in which the NRT gene or the NR gene is deleted or expression thereof is downregulated, nitric acid assimilation is reduced in several cases. In such a case, the transformant is preferably cultured in a culture medium containing urea, ammonia, nitrous acid or the like as a nitrogen source.

The concentration of the nitrogen source contained in a culture medium can be appropriately set. Specifically, the concentration of the nitrogen source is, as equivalent amount of nitrogen atom, preferably 1 mg/L or more, more preferably 5 mg/L or more, and further preferably 10 mg/L or more. The upper limit thereof is preferably 2,000 mg/L, more preferably 1,000 mg/L, further preferably 500 mg/L, and furthermore preferably 200 mg/L.

{0039}

With regard to the embodiments described above, the present invention also discloses methods of improving resistance to a substrate analog of nitric acid in a microalga, and transformants, described below.

{0040}

<1> A method of improving resistance to a substrate analog of nitric acid in a microalga, containing deleting a gene encoding the following protein (A) or (B) present in the genome of the microalga, or downregulating expression of a gene encoding the following protein (A) or (B):

(A) a protein consisting of the amino acid sequence set forth in SEQ ID NO: 41; and (B) a protein consisting of an amino acid sequence having 70% or more, preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (A), and having NRT activity.

<2> A method of improving resistance to a substrate analog of nitric acid in a microalga, containing deleting a gene or downregulating gene expression for each a gene encoding the following protein (A) or (B) and a gene encoding the following protein (C) or (D) present in the genome of the microalga:

(A) a protein consisting of the amino acid sequence set forth in SEQ ID NO: 41;

(B) a protein consisting of an amino acid sequence having 70% or more, preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (A), and having NRT activity;

(C) a protein consisting of the amino acid sequence set forth in SEQ ID NO: 42; and (D) a protein consisting of an amino acid sequence having 70% or more, preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (C), and having NR activity.

{0041}

<3> A transformant of a microalga having resistance to a substrate analog of nitric acid, wherein a gene encoding the protein (A) or (B) present in the genome is deleted, or expression of a gene encoding the protein (A) or (B) is downregulated.

<4> A transformant of a microalga having resistance to a substrate analog of nitric acid, wherein a gene is deleted or gene expression is downregulated for each a gene encoding the protein (A) or (B) and a gene encoding the protein (C) or (D) present in the genome.

{0042}

<5> A method of preparing a transformant having resistance to a substrate analog of nitric acid, containing:

deleting a gene encoding the protein (A) or (B) present in the genome of a microalga, or downregulating expression of a gene encoding the protein (A) or (B); and obtaining the transformant using resistance to the substrate analog of nitric acid as an indicator.

<6> A method of preparing a transformant having resistance to a substrate analog of nitric acid, containing:

deleting a gene or downregulating gene expression for each a gene encoding the protein (A) or (B) and a gene encoding the protein (C) or (D) present in the genome of a microalga; and obtaining the transformant using resistance to the substrate analog of nitric acid as an indicator.

{0043}

<7> The method or the transformant described in any one of the above items <1> to <6>, wherein the substrate analog of nitric acid is chloric acid.

<8> The method or the transformant described in any one of the above items <1> to <7>, wherein the transformant can be grown in a medium containing 3 mM or more, preferably 5 mM or more of chloric acid or a salt thereof for one week or more, preferably 2 weeks or more, and 8 weeks or less.

<9> The method or the transformant described in any one of the above items <1> to <8>, wherein the transformant is cultured in a medium containing at least one kind selected from the group consisting of urea, ammonia, and nitrous acid, as nitrogen sources.

<10> The method or the transformant described in the above item <9>, wherein concentration of the nitrogen source contained in the medium is, as equivalent amount of nitrogen atom, 1 mg/L or more, preferably 5 mg/L or more, more preferably 10 mg/L or more, and 2,000 mg/L or less, preferably 1,000 mg/L or less, more preferably 500 mg/L or less, and further preferably 200 mg/L or less.

{0044}

<11> The method or the transformant described in any one of the above items <1> to <10>, wherein the protein (B) consists of an amino acid sequence in which 1 or several, preferably 1 or more and 141 or less, more preferably 1 or more and 117 or less, further preferably 1 or more and 94 or less, furthermore preferably 1 or more and 71 or less, furthermore preferably 1 or more and 47 or less, furthermore preferably 1 or more and 38 or less, furthermore preferably 1 or more and 24 or less, furthermore preferably 1 or more and 10 or less, and furthermore preferably 1 or more and 5 or less amino acids are deleted, substituted, inserted or added to the amino acid sequence of the protein (A).

<12> The method or the transformant described in any one of the above items <1> to <11>, wherein the gene encoding the protein (A) or (B) is a gene consisting of the following DNA (a) or (b):

(a) a DNA consisting of the nucleotide sequence set forth in SEQ ID NO: 39; and (b) a DNA consisting of a nucleotide sequence having 55% or more, preferably 60% or more, more preferably 65% or more, further preferably 70% or more, furthermore preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence of the DNA (a), and encoding a protein having NRT activity.

<13> The method or the transformant described in the above item <12>, wherein the DNA (b) is a DNA consisting of a nucleotide sequence in which 1 or several, preferably 1 or more and 634 or less, more preferably 1 or more and 563 or less, further preferably 1 or more and 493 or less, furthermore preferably 1 or more and 423 or less, furthermore preferably 1 or more and 352 or less, furthermore preferably 1 or more and 282 or less, furthermore preferably 1 or more and 212 or less, furthermore preferably 1 or more and 141 or less, furthermore preferably 1 or more and 113 or less, furthermore preferably 1 or more and 71 or less, furthermore preferably 1 or more and 29 or less, and furthermore preferably 1 or more and or 15 less nucleotides, are deleted, substituted, inserted or added to the nucleotide sequence of the DNA (a), and encoding a protein having NRT activity, or a DNA capable of hybridizing with a DNA consisting of the nucleotide sequence complementary with the DNA (a) under a stringent condition, and encoding a protein having NRT activity.

{0045}

<14> The method or the transformant described in any one of the above items <2>, <4>, and <6> to <13>, wherein the protein (D) consists of an amino acid sequence in which 1 or several, preferably 1 or more and 523 or less, more preferably 1 or more and 457 or less, further preferably 1 or more and 392 or less, furthermore preferably 1 or more and 327 or less, furthermore preferably 1 or more and 261 or less, furthermore preferably 1 or more and 196 or less, furthermore preferably 1 or more and 130 or less, furthermore preferably 1 or more and 104 or less, furthermore preferably 1 or more and 65 or less, furthermore preferably 1 or more and 26 or less, and furthermore preferably 1 or more and 13 or less amino acids are deleted, substituted, inserted or added to the amino acid sequence of the protein (C).

<15> The method or the transformant described in any one of the above items <2>, <4>, and <6> to <14>, wherein the gene encoding the protein (C) or (D) is a gene consisting of the following DNA (c) or (d):

(c) a DNA consisting of the nucleotide sequence set forth in SEQ ID NO: 40; and (d) a DNA consisting of a nucleotide sequence having 70% or more, preferably 75% or more, more preferably 80% or more, further preferably 85% or more, furthermore preferably 90% or more, furthermore preferably 92% or more, furthermore preferably 95% or more, furthermore preferably 98% or more, and furthermore preferably 99% or more identity with the nucleotide sequence of the DNA (c), and encoding a protein having NR activity.

<16> The method or the transformant described in the above item <15>, wherein the DNA (d) is a DNA consisting of a nucleotide sequence in which 1 or several, preferably 1 or more and 764 or less, more preferably 1 or more and 636 or less, further preferably 1 or more and 509 or less, furthermore preferably 1 or more and 382 or less, furthermore preferably 1 or more and 255 or less, furthermore preferably 1 or more and 204 or less, furthermore preferably 1 or more and 128 or less, furthermore preferably 1 or more and 51 or less, and furthermore preferably 1 or more and 26 or less nucleotides, are deleted, substituted, inserted or added to the nucleotide sequence of the DNA (c), and encoding a protein having NR activity, or a DNA capable of hybridizing with a DNA consisting of the nucleotide sequence complementary with the DNA (c) under a stringent condition, and encoding a protein having NR activity.

{0046}

<17> The method or the transformant described in any one of the above items <1> to <16>, wherein the microalga is a microalga of the class Eustigmatophyceae, preferably a microalga of the order Eustigmatales, more preferably a microalga of the genus *Nannochloropsis*.

<18> The method or the transformant described in any one of the above items <1> to <17>, wherein the microalga is selected from the group consisting of *Nannochloropsis oculata, Nannochloropsis oceanica, Nannochloropsis gaditana, Nannochloropsis salina, Nannochloropsis atomus, Nannochloropsis maculata, Nannochloropsis granulata*, and *Nannochloropsis* sp., preferably selected from the group consisting of *Nannochloropsis oculata, Nannochloropsis oceanica*, and *Nannochloropsis* gaditana, more preferably *Nannochloropsis oculata*.

EXAMPLES

{0047}

Hereinafter, the present invention will be described more in detail with reference to Examples, but the present invention is not limited thereto. Herein, the nucleotide sequences of the primers used in Examples are shown in Table 1.

{0048}

TABLE 1

| Primer No. | Nucleotide Sequence | SEQ ID NO: |
|---|---|---|
| 2 | atggccaagctgaccagcgc | SEQ ID NO: 2 |
| 3 | ttagtcctgctcctcggcca | SEQ ID NO: 3 |
| 4 | acacaggaaacagctggcgg tcttttgtcctttcc | SEQ ID NO: 4 |

TABLE 1-continued

| Primer No. | Nucleotide Sequence | SEQ ID NO: |
|---|---|---|
| 5 | ggtcagcttggccataatct gctcggaggggagga | SEQ ID NO: 5 |
| 6 | gaggagcaggactaagcttc tgtggaagagccagt | SEQ ID NO: 6 |
| 7 | tcggggctggcttaactgat cttgtccatctcgtg | SEQ ID NO: 7 |
| 10 | agctgtttcctgtgtgaaat tgttatccgctc | SEQ ID NO: 10 |
| 11 | ttaagccagccccgacaccc gccaacaccgctg | SEQ ID NO: 11 |
| 12 | acacaggaaacagctcctgg gaaatgtgccattg | SEQ ID NO: 12 |
| 13 | ggacaaaagaccgccacgtg ttccttctgagaaag | SEQ ID NO: 13 |
| 14 | gatggacaagatcagtttat gtcagacgcaaggtc | SEQ ID NO: 14 |
| 15 | tcggggctggcttaacata actggatgacaatgagcac aag | SEQ ID NO: 15 |
| 16 | acacaggaaacagctcagt acagacgcgcgagacg | SEQ ID NO: 16 |
| 17 | ggacaaaagaccgccgatt ccaaatacgccagcac | SEQ ID NO: 17 |
| 18 | gatggacaagatcagcatc catctctatctttacc | SEQ ID NO: 18 |
| 19 | tcggggctggcttaacagt cactagcgacgtattc | SEQ ID NO: 19 |
| 25 | ggcggtcttttgtcctttc ctctatagcccgc | SEQ ID NO: 25 |
| 26 | ctgatcttgtccatctcgt gtgccacgggtggca | SEQ ID NO: 26 |
| 27 | cctgggaaatgtgccattg taaggag | SEQ ID NO: 27 |
| 28 | cataactggatgacaatga gcacaag | SEQ ID NO: 28 |
| 29 | cagtacagacgcgc gagacg | SEQ ID NO: 29 |
| 30 | cagtcactagcgac gtattc | SEQ ID NO: 30 |
| 31 | gtgccgcagcagctttagc acgttg | SEQ ID NO: 31 |
| 32 | agtgtcgcaaggattctct aacacg | SEQ ID NO: 32 |
| 33 | gacgtgaccctgttcatcag | SEQ ID NO: 33 |
| 34 | tgcacgacaggcgacattcg | SEQ ID NO: 34 |
| 35 | gcacagctcacagcgctca ttgcaatc | SEQ ID NO: 35 |
| 36 | ttaaaagatgaaaaactgg tcctcggtgtaacc | SEQ ID NO: 36 |
| 37 | agatagagatggatgacgt gttccttctgagaaag | SEQ ID NO: 37 |

TABLE 1-continued

| Primer No. | Nucleotide Sequence | SEQ ID NO: |
|---|---|---|
| 38 | catccatctctatctttac ctgtgtctatg | SEQ ID NO: 38 |

{0049}

Example 1 Providing Chloric Acid Resistance for *Nannochloropsis oculata*

(1) Construction of Plasmid for Zeocin Resistance Gene Expression

A zeocin resistance gene (SEQ ID NO: 1) was artificially synthesized. Using the thus-synthesized DNA fragments as a template, and a pair of the primer Nos. 2 and 3 shown in Table 1, PCR was carried out, to amplify the zeocin resistance gene.

Further, using a genome of *Nannochloropsis oculata* strain NIES-2145 (obtained from National Institute for Environmental Studies (NIES)) as a template, and a pair of the primer Nos. 4 and 5, and a pair of the primer Nos. 6 and 7 shown in Table 1, respectively, PCRs were carried out to amplify the VCP1 promoter sequence (SEQ ID NO: 8) and the VCP1 terminator sequence (SEQ ID NO: 9).

Furthermore, using a plasmid vector pUC118 (manufactured by Takara Bio) as a template, and a pair of the primer Nos. 10 and 11 shown in Table 1, PCR was carried out to amplify the plasmid vector pUC118.

The thus-obtained four fragments were fused using an In-Fusion HD Cloning Kit (manufactured by Clontech) to construct a plasmid for zeocin resistance gene expression.

{0050}

(2) Construction of Plasmid for Homologous Recombination of Endogenous NRT Gene and NR Gene in *Nannochloropsis*

Using a genomic DNA extracted from *Nannochloropsis oculata* strain NIES-2145 as a template, and pairs of the primer Nos. 12 and 13, pairs of the primer Nos. 14 and 15, pairs of the primer Nos. 16 and 17, and pairs of the primer Nos. 18 and 19 shown in Table 1 respectively, PCRs were carried out to amplify the partial sequences (genome sequence (W) (the nucleotide sequence of the $2254^{th}$ to $3849^{th}$ nucleotides of SEQ ID NO: 20 (SEQ ID NO: 21)), genome sequence (X) (the nucleotide sequence of the $5969^{th}$ to $7479^{th}$ nucleotides of SEQ ID NO: 20 (SEQ ID NO: 22)), genome sequence (Y) (the nucleotide sequence of the $6816^{th}$ to $8286^{th}$ nucleotides of SEQ ID NO: 20 (SEQ ID NO: 23)), and genome sequence (Z) (the nucleotide sequence of the $8516^{th}$ to $10053^{rd}$ nucleotides of SEQ ID NO: 20 (SEQ ID NO: 24))) of the genome sequence (SEQ ID NO: 20) around the NRT gene and the NR gene (hereinafter, also referred to as "NRT-NR gene"), shown in FIG. 2.

Further, using the plasmid for the zeocin resistance gene expression, and a pair of the primer Nos. 25 and 26 shown in Table 1, PCR was carried out to obtain a cassette for the zeocin resistance gene expression, Pvcp1-ble-Tvcp1.

{0051}

After that, a plasmid for homologous recombination of the NRT gene (hereinafter, also referred to as "plasmid for the NRT gene KO") was constructed by fusing the obtained fragment of genome sequence (W), the fragment of genome sequence (X), the cassette for zeocin resistance gene expression, and the plasmid vector pUC118, by using In-Fusion HD Cloning Kit (manufactured by Clontech).

Similarly, a plasmid for homologous recombination of the NR gene (hereinafter, also referred to as "plasmid for the NR gene KO") was constructed by fusing the obtained fragment of genome sequence (Y), the fragment of genome sequence (Z), the fragment of the cassette for zeocin resistance gene expression, and the plasmid vector pUC118.

Further, a plasmid for homologous recombination of the NRT-NR gene (1) (hereinafter, also referred to as "plasmid for the NRT-NR gene KO (1)") was constructed by fusing the obtained fragment of genome sequence (W), the fragment of genome sequence (Z), the fragment of the cassette for zeocin resistance gene expression, and the plasmid vector pUC118.

Herein, these plasmids consisted of the pUC118 vector sequence and an insert sequence in which the upstream genome sequence of the sequence set forth in SEQ ID NO: 20 (fragment of the genome sequence (W) or fragment of the genome sequence (Y)), the VCP1 promoter sequence, the zeocin resistance gene, the VCP1 terminator sequence, and the downstream genome sequence of the sequence set forth in SEQ ID NO: 20 (fragment of the genome sequence (X) or fragment of the genome sequence (Z)) were linked in this order (see FIG. 3A to 3C).

{0052}

(3) Introduction of a Plasmid for Homologous Recombination into *Nannochloropsis oculata*

By using the above-described plasmid for homologous recombination of the NRT gene as a template, and a pair of the primer Nos. 27 and 28 shown in Table 1, PCR was carried out to amplify a cassette for homologous recombination of the NRT gene (an insertion sequence shown in FIG. 3A).

Similarly, by using the above-described plasmid for homologous recombination of the NR gene as a template, and a pair of the primer Nos. 29 and 30 shown in Table 1, PCR was carried out to amplify a cassette for homologous recombination of the NR gene (an insertion sequence shown in FIG. 3B).

Further, by using the above-described plasmid for homologous recombination of the NRT-NR gene (1) as a template, and a pair of the primer Nos. 27 and 30 shown in Table 1, PCR was carried out to amplify a cassette for homologous recombination of the NRT-NR gene (1) (an insertion sequence shown in FIG. 3C).

Each of the thus-amplified DNA fragments was purified using High Pure PCR Product Purification Kit (manufactured by Roche Applied Science).

{0053}

The cultured *Nannochloropsis oculata* strain NIES-2145 was centrifuged and collected, and washed with a 384 mM of sorbitol solution, whereby cell fluid in which the resulting material was suspended with sorbitol was used as a host.

Three types of the amplified cassettes for homologous recombination described above were mixed by about 500 ng with the host cell respectively, and electroporation was carried out under the conditions of 50 μF, 500Ω and 2,200 v/2 mm.

Recovery cultivation was performed for 24 hours in urea liquid medium (400 mg of urea, 30 mg of $NaH_2PO_4 \cdot 2H_2O$, 0.5 μg of vitamin B12, 0.5 μg of biotin, 100 μg of thiamine, 10 mg of $Na_2SiO_3 \cdot 9H_2O$, 4.4 mg of $Na_2EDTA \cdot 2H_2O$, 3.16 mg of $FeCl_3 \cdot 6H_2O$, 12 μg of $CoCl_2 \cdot 6H_2O$, 21 μg of $ZnSO_4 \cdot 7H_2O$, 180 μg of $MnCl_2 \cdot 4H_2O$, 7 μg of $CuSO_4 \cdot 5H_2O$, 7 μg of $Na_2MoO_4 \cdot 2H_2O$/artificial sea water 1 L) (hereinafter, referred to as "urea medium"). After that, the resultant was inoculated in urea agar medium containing 2

μg/mL of zeocin, and cultured for two to three weeks under 12 h/12 h light-dark conditions at 25° C. under an atmosphere of 0.3% $CO_2$.

{0054}

(4) Selection of NR Gene-Disrupted Strain, NRT Gene-Disrupted Strain, and NRT Gene and NR Gene-Disrupted Strain From colonies obtained using zeocin resistance as an indicator, strains in which the NR gene, the NRT gene or the NRT-NR gene of *Nannochloropsis oculata* was disrupted by the cassette for homologous recombination were selected by PCR, respectively.

{0055}

The NR gene-disrupted strain (hereinafter, also referred to as "ΔNR strain") can be obtained by causing recombination using the homologous sequences between the genomic DNA of the wild-type (WT) strain and the cassette for homologous recombination of the NR gene (NR-KO fragment) to disrupt the NR gene encoded in the genome, as shown in FIG. 4A.

The ΔNR strain was selected by performing PCR by using a pair of the primer Nos. 31 and 32 shown in Table 1, and using a difference in lengths of fragments to be amplified as an indicator (see FIGS. 4B and 4C).

As shown in FIG. 4C, amplification of a gene fragment of about 3.4 kbp was confirmed in the WT strain. On the other hand, amplification of a gene fragment of about 5.0 kbp was confirmed in the ΔNR strain.

{0056}

The NRT gene-disrupted strain (hereinafter, also referred to as "ΔNRT strain") can be obtained by causing recombination using the homologous sequences between the genomic DNA of the WT strain and the cassette for homologous recombination of the NRT gene (NRT-KO fragment) to disrupt the NRT gene encoded in the genome, as shown in FIG. 5A.

The ΔNRT strain was selected by performing PCR by using a pair of the primer Nos. 33 and 34 shown in Table 1, and using existence or nonexistence of amplified fragment as an indicator (see FIGS. 5B and 5C).

As shown in FIG. 5C, no amplification of a gene fragment was confirmed in the WT strain. On the contrary, amplification of a gene fragment of about 3.3 kbp was confirmed in the ΔNR strain.

{0057}

The NRT-NR gene-disrupted strain (hereinafter, also referred to as "ΔNRTΔNR strain") can be obtained by causing recombination using the homologous sequences between the genomic DNA of the WT strain and the cassette for homologous recombination of the NRT-NR gene (1) (NRT-NR-KO fragment) to disrupt the NRT gene and the NR gene encoded in the genome, as shown in FIG. 6A.

The ΔNRTΔNR strain was selected by performing PCR by using a pair of the primer Nos. 35 and 36 shown in Table 1, and using a difference in lengths of fragments to be amplified as an indicator (see FIGS. 6B and 6C).

As shown in FIG. 6C, amplification of a gene fragment of about 6.9 kbp was confirmed in the WT strain. On the other hand, amplification of a gene fragment of about 4.1 kbp was confirmed in the ΔNRTΔNR strain.

{0058}

(5) Chloric Acid Resistance Evaluation of ΔNR Strain, ΔNRT Strain, and ΔNRTΔNR Strain The ΔNR strain, the ΔNRT strain, and the ΔNRTΔNR strain were inoculated respectively to the three kinds of agar media of urea agar media, nitric acid agar media in which urea being nitrogen source of urea agar media was replaced with nitric acid (1.1 g of nitric acid, 30 mg of $NaH_2PO_4 \cdot 2H_2O$, 0.5 µg of vitamin B12, 0.5 µg of biotin, 100 µg of thiamine, 10 mg of $Na_2SiO_3 \cdot 9H_2O$, 4.4 mg of $Na_2EDTA \cdot 2H_2O$, 3.16 mg of $FeCl_3 \cdot 6H_2O$, 12 µg of $CoCl_2 \cdot 6H_2O$, 21 µg of $ZnSO_4 \cdot 7H_2O$, 180 µg of $MnCl_2 \cdot 4H_2O$, 7 µg of $CuSO_4 \cdot 5H_2O$, 7 µg of $Na_2MoO_4 \cdot 2H_2O$/artificial sea water 1 L), and urea agar media containing 5 mM of potassium chlorate ($KClO_3$). After that, the resultants were cultured for two to three weeks under 12 h/12 h light-dark conditions at 25° C. under an atmosphere of 0.3% $CO_2$.

{0059}

FIG. 7 shows an aspect of an agar medium after culture.

As shown in FIG. 7, when the nitric acid agar medium was used, growth was able to be achieved only for the WT strain, but growth was unable to be confirmed for the ΔNR strain, the ΔNRT strain and the ΔNRTΔNR strain. On the other hand, growth on the urea agar medium was able to be achieved for all the WT strain, the ΔNR strain, the ΔNRT strain and the ΔNRTΔNR strain. From these results, when the NRT gene or the NR gene was disrupted in the algae belonging to the genus *Nannochloropsis*, property of nitric acid assimilation is lost. Moreover, these results show that *Nannochloropsis* can also use urea as the nitrogen source in place of nitric acid.

{0060}

Moreover, as mentioned above, it is generally known that chloric acid is converted by NR to exhibit cytotoxicity. Therefore, sensitivity of *Nannochloropsis* to chloric acid was evaluated by comparing growth of the WT strain, the ΔNR strain, the ΔNRT strain and the ΔNRTΔNR strain on a chloric acid-containing agar medium.

As a result, as shown in the lower part of FIG. 7, the WT strain was killed by exposure to chloric acid. In addition, viability was also evaluated on the strain (ΔNR strain) in which expression of the NR gene was downregulated as generally stated, but growth was unable to be confirmed under conditions of 5 mM chloric acid, and the chloric acid resistance was unable to be improved only by disruption of the NR gene. On the other hand, growth was also confirmed in the ΔNRT strain under conditions of exposure to chloric acid, and it was confirmed that the chloric acid resistance is improved by suppression of the NRT activity in comparison with the WT strain. Further, more favorable growth was observed in the ΔNRTΔNR strain even in comparison with the ΔNRT strain, and it was indicated that both activities of the NRT and the NR are suppressed, whereby the chloric acid resistance is significantly improved.

Further, viability of the WT strain, the ΔNR strain, the ΔNRT strain and the ΔNRTΔNR strain was evaluated by changing a concentration of potassium chlorate to be added to the urea agar medium according to the same method as mentioned above (3 weeks after spot). In addition, the viability was evaluated by the following evaluation criteria:

(Evaluation Criteria)

−: Not grown

+: Suppressed in growth, (somewhat) dye fading

++: Suppressed in growth

+++: Fully grown

Table 2 shows the results.

{0062}

TABLE 2

| $KClO_3$ concentration | WT strain | ΔNR strain | ΔNRT strain | ΔNRTΔNR strain |
|---|---|---|---|---|
| 0 mM | +++ | +++ | +++ | +++ |
| 5 mM | − | − | ++ | +++ |
| 10 mM | − | − | − | +++ |
| 15 mM | − | − | − | +++ |
| 20 mM | − | − | − | ++ |
| 30 mM | − | − | − | + |

{0063}

As shown in Table 2, growth was confirmed in the ΔNRT strain even under conditions of 5 mM chloric acid concentration, and it was confirmed that the chloric acid resistance is improved by suppression of the NRT activity in comparison with the WT strain or the ΔNR strain. Further, the chloric acid resistance was significantly improved in the ΔNRTΔNR strain, and growth was able to be achieved even under conditions of 30 mM chloric acid concentration.

{0064}

As described above, in the class Eustigmatophyceae, the NRT gene is deleted or expression of the NRT gene is downregulated, whereby resistance to the substrate analog of nitric acid, such as chloric acid, can be improved.

Further, in addition to the NRT gene, the NR gene is deleted or expression of the NR gene is downregulated, whereby the resistance to the substrate analog of nitric acid is markedly improved, and therefore the transformant capable of growing even in the presence of chloric acid with high concentration can be prepared.

{0065}

Example 2 Obtaining a ΔNRTΔNR Strain by Using an Indicator of Chloric Acid Resistance of *Nannochloropsis oculata*

(1) Construction of Plasmid for Homologous Recombination of Endogenous NRT-NR Gene in *Nannochloropsis*

By using the plasmid for the NRT-NR gene KO (1) prepared in Example 1 (see FIG. 3C) as a template, and pairs of the primer Nos. 37 and 38 shown in Table 1, PCR was carried out to amplify a fragment in which the partial sequences (genome sequence (W) (SEQ ID NO: 21), and genome sequence (Z) (SEQ ID NO: 24)) of the genome sequence around the NRT-NR gene (SEQ ID NO: 20) shown in FIG. 2 was linked with the pUC118 vector sequence.

The thus-amplified fragment was fused by a method similar to that described in Example 1, whereby a plasmid for homologous recombination of the NRT-NR gene (2) without a cassette for drug resistance gene (ble) expression (hereinafter, also referred to as "plasmid for NRT-NR gene KO (2)") was constructed.

Herein, the expression plasmid consisted of the pUC118 vector sequence and an insert sequence in which the genome sequence (W) and genome sequence (Z) of *Nannochloropsis oculata* strain NIES-2145 shown in FIG. 2 were linked in this order (see FIG. 8A).

{0066}

(2) Introduction of Plasmid for Homologous Recombination into *Nannochloropsis oculata*

By using the above-described plasmid for homologous recombination of the NRT-NR gene (2) as a template, and a pair of the primer Nos. 27 and 30 shown in Table 1, PCR was carried out to amplify a cassette for homologous recombination of the NRT-NR gene (2) (an insertion sequence shown in FIG. 8A).

The thus-amplified DNA fragment was introduced into *Nannochloropsis oculata* by a method similar to that described in Example 1, and then recovery cultivation was performed. After the recovery cultivation, the resultant was inoculated in an urea agar medium containing 20 mM of potassium chlorate ($KClO_3$), cultured for two to three weeks under 12 h/12 h light-dark conditions at 25° C. under an atmosphere of 0.3% $CO_2$, and colony was obtained by using an indicator of chloric acid resistance.

{0067}
(3) Analysis of the Genome Around the NRT-NR Gene of Chloric Acid-Resistant Strain The genome around the NRT-NR gene was confirmed in the transformant which was obtained by using an indicator of chloric acid resistance.

By using a pair of the primer Nos. 35 and 36 shown in Table 1, PCR was carried out to amplify the genome around the NRT-NR gene. As a result, fragments of about 2.2 kbp were amplified in all strains which were obtained by using the indicator of chloric acid resistance.

As shown in FIG. 8B, when homologous recombination occurs with the genomic DNA of the WT strain in a homologous sequence site of the above-described cassette for homologous recombination of the NRT-NR gene (2) (NRT-NR-KO fragments (2)), the ΔNRTΔNR strain is obtained. Thus, with regard to the fragments to be amplified by PCR under the above-described conditions, fragments of about 6.9 kbp are amplified in the WT strain, and fragments of about 2.2 kbp are amplified in the ΔNRTΔNR strain (see FIGS. 8C and 8D).

{0068}
From the results described above, it was revealed that all the strains which were obtained using the chloric acid resistance as the indicator are the ΔNRTΔNR strains. This finding indicates that the transformant can also be obtained by using the chloric acid resistance as the indicator.

{0069}
Having described our invention as related to the present embodiments, it is our intention that the invention not be limited by any of the details of the description, unless otherwise specified, but rather be construed broadly within its spirit and scope as set out in the accompanying claims.

{0070}
This application claims priority on Patent Application No. 2017-078886 filed in Japan on Apr. 12, 2017, which is entirely herein incorporated by reference.

---

What is claimed is:

1. A method of improving resistance to a substrate analog of nitric acid in a *Nannochloropsis* microalga, comprising:

deleting a gene encoding the following protein (A) or (B) from the genome of the *Nannochloropsis* microalga:

wherein protein (A) is:

(A) a protein consisting of the amino acid sequence set forth in SEQ ID NO: 41; and wherein protein (B) is:

(B) a protein consisting of an amino acid sequence having 92% or more identity with the amino acid sequence of the protein (A);

and wherein the substrate analog of nitric acid is chloric acid.

2. The method of claim 1, further comprising:

deleting a gene encoding the following protein (C) or (D) from the genome of the microalga: wherein protein (C) is:

(C) a protein consisting of the amino acid sequence set forth in SEQ ID NO: 42; and wherein protein (D) is:

(D) a protein consisting of an amino acid sequence having 92% or more identity with the amino acid sequence of the protein (C).

3. The method according to claim 2, wherein a protein consisting of the amino acid sequence set forth in SEQ ID NO: 41 is deleted and a protein consisting of the amino acid sequence set forth in SEQ ID NO: 42 is deleted.

4. The method according to claim 1, wherein the microalga is selected from the group consisting of *Nannochloropsis oculata, Nannochloropsis granulata* and *Nannochloropsis* oceanica.

5. A transformant of a *Nannochloropsis* microalga having resistance to a substrate analog of nitric acid, wherein a gene encoding the following protein (A) or (B) is deleted from the genome of the transformant, or expression of the gene encoding the following protein (A) or (B) is downregulated in the transformant:

wherein protein (A) is:

(A) a protein consisting of the amino acid sequence set forth in SEQ ID NO: 41; and wherein protein (B) is:

(B) a protein consisting of an amino acid sequence having 92% or more identity with the amino acid sequence of the protein (A);

and wherein the substrate analog of nitric acid is chloric acid.

6. The transformant of claim 5, wherein a gene encoding the following protein (C) or (D) is deleted from the genome of the transformant;

wherein protein (C) is:

(C) a protein consisting of the amino acid sequence set forth in SEQ ID NO: 42; and wherein protein (D) is:

(D) a protein consisting of an amino acid sequence having 92% or more identity with the amino acid sequence of the protein (C).

7. The transformant according to claim 5, wherein the microalga is selected from the group consisting of *Nannochloropsis oculata, Nannochloropsis granulata* and *Nannochloropsis* oceanica.

8. A method of preparing a transformant having resistance to a substrate analog of nitric acid, comprising:

deleting a gene encoding the following protein (A) or (B) from the genome of a *Nannochloropsis* microalga; and obtaining the transformant using resistance to the substrate analog of nitric acid as an indicator:

wherein protein (A) is:

(A) a protein consisting of the amino acid sequence set forth in SEQ ID NO: 41; and wherein protein (B) is:

(B) a protein consisting of an amino acid sequence having 92% or more identity with the amino acid sequence of the protein (A);

and wherein the substrate analog of nitric acid is chloric acid.

9. The method of claim 8, further comprising:

deleting a gene encoding the following protein (C) or (D) from the genome of the microalga; and obtaining the transformant using resistance to the substrate analog of nitric acid as an indicator:

wherein protein (C) is:

(C) a protein consisting of the amino acid sequence set forth in SEQ ID NO: 42; and wherein protein (D) is:

(D) a protein consisting of an amino acid sequence having 92% or more identity with the amino acid sequence of the protein (C).

10. The method of claim 8, wherein the microalga is selected from the group consisting of *Nannochloropsis oculata, Nannochloropsis granulata* and *Nannochloropsis* oceanica.

11. A method of improving resistance to a substrate analog of nitric acid in a *Nannochloropsis* microalga, comprising:

deleting a gene encoding the following protein (A) or (B) from the genome of the *Nannochloropsis* microalga:

wherein protein (A) is:

(A) a protein consisting of the amino acid sequence set forth in SEQ ID NO: 41; and wherein protein (B) is:

(B) a protein consisting of an amino acid sequence having 95% or more identity with the amino acid sequence of the protein (A);

and wherein the substrate analog of nitric acid is chloric acid.

12. A transformant of a *Nannochloropsis* microalga having resistance to a substrate analog of nitric acid, wherein a gene encoding the following protein (A) or (B) is deleted from the genome of the transformant:

wherein protein (A) is:

(A) a protein consisting of the amino acid sequence set forth in SEQ ID NO: 41; and wherein protein (B) is:

(B) a protein consisting of an amino acid sequence having 95% or more identity with the amino acid sequence of the protein (A);

and wherein the substrate analog of nitric acid is chloric acid.

13. A method of preparing a transformant having resistance to a substrate analog of nitric acid, comprising:

deleting a gene encoding the following protein (A) or (B) from the genome of a *Nannochloropsis* microalga; and obtaining the transformant using resistance to the substrate analog of nitric acid as an indicator:

wherein protein (A) is:

(A) a protein consisting of the amino acid sequence set forth in SEQ ID NO: 41; and wherein protein (B) is:

(B) a protein consisting of an amino acid sequence having 95% or more identity with the amino acid sequence of the protein (A);

and wherein the substrate analog of nitric acid is chloric acid.

* * * * *

SEQUENCE LISTING

```
<160> NUMBER OF SEQ ID NOS: 42

<210> SEQ ID NO 1
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 1
atggccaagc tgaccagcgc cgttccggtg ctcaccgcgc gcgacgtcgc cggagcggtc        60
gagttctgga ccgaccggct cgggttctcc cgggacttcg tggaggacga cttcgccggt       120
gtggtccggg acgacgtgac cctgttcatc agcgcggtcc aggaccaggt ggtgccggac       180
aacaccctgg cctgggtgtg ggtgcgcggc ctggacgagc tgtacgccga gtggtcggag       240
gtcgtgtcca cgaacttccg ggacgcctcc gggccggcca tgaccgagat cggcgagcag       300
ccgtgggggc gggagttcgc cctgcgcgac ccggccggca actgcgtgca cttcgtggcc       360
gaggagcagg actaa                                                        375

<210> SEQ ID NO 2
<211> LENGTH: 20
<212> TYPE: DNA
<213> ORGANISM: Artificial Sequence
<220> FEATURE:
<223> OTHER INFORMATION: Primer No. 2

<400> SEQUENCE: 2
atggccaagc tgaccagcgc                                                    20

<210> SEQ ID NO 3
<211> LENGTH: 20
<212> TYPE: DNA
<213> ORGANISM: Artificial Sequence
<220> FEATURE:
<223> OTHER INFORMATION: Primer No. 3

<400> SEQUENCE: 3
```
ttagtcctgc tcctcggcca                                                          20

<210> SEQ ID NO 4
<211> LENGTH: 35
<212> TYPE: DNA
<213> ORGANISM: Artificial Sequence
<220> FEATURE:
<223> OTHER INFORMATION: Primer No. 4

<400> SEQUENCE: 4
acacaggaaa cagctggcgg tcttttgtcc tttcc                                         35

<210> SEQ ID NO 5
<211> LENGTH: 35
<212> TYPE: DNA
<213> ORGANISM: Artificial Sequence
<220> FEATURE:
<223> OTHER INFORMATION: Primer No. 5

<400> SEQUENCE: 5
ggtcagcttg gccataatct gctcggaggg gagga                                         35

<210> SEQ ID NO 6
<211> LENGTH: 35
<212> TYPE: DNA
<213> ORGANISM: Artificial Sequence
<220> FEATURE:
<223> OTHER INFORMATION: Primer No. 6

<400> SEQUENCE: 6
gaggagcagg actaagcttc tgtggaagag ccagt                                         35

<210> SEQ ID NO 7
<211> LENGTH: 35
<212> TYPE: DNA
<213> ORGANISM: Artificial Sequence
<220> FEATURE:
<223> OTHER INFORMATION: Primer No. 7

<400> SEQUENCE: 7
tcggggctgg cttaactgat cttgtccatc tcgtg                                         35

<210> SEQ ID NO 8
<211> LENGTH: 802
<212> TYPE: DNA
<213> ORGANISM: Nannochloropsis oculata

<400> SEQUENCE: 8
ggcggtcttt tgtcctttcc tctatagccc gcccgtctag agggcacacg cgatgatctt      60
tatatctctt catgtgtctt tgttttaact aggatactgc cgggtgaatg cccatcggac      120
aagaggccaa actctatcta cacccttttg acttctgttg tggtcgtagt gtgtgcttgc      180
atgccctgaa agtccaggca tcccacttgt gctctaaccc cattcaaaac agcagaagtg      240
cttaattaag atatagattc atgatctcct gtccctcct tcttaccttt tcacaaacct       300
cacacagaag tctccactct tcgcctctaa aacctctttt taaattatgg taagttcgtg      360
cggcagtggg ttttcggatc tatatttgtc aagatccagt tcaaggtcag ggatgtagat      420
taagtacaga aggagaagca caagcgcgcc agttcgcccc tcacggcctg gagcagggca      480
tttaatccct ctatcttacc agaaccatac tatacaacca atcctgttgg catcgctctg      540
tctatttgtc gtgcgtgcat gtgtccatgg tgtggtgggg ggcaggggtt ttcggggttg      600

-continued

```
cggttgaagg caccttatca gaaagatgcc ctcagagata gaggtagccc cctcccccg      660 atcttcgacc agtcctgtca ggcgaacact ttcacccgtc gttcacctcg ttacacacaa      720
ggagtagacc tctgaagttc taattgtcat aaatgcccct cccccctccc tctttccctt      780
gatcctcccc tccgagcaga tt                                             802
```

```
<210> SEQ ID NO 9
<211> LENGTH: 643
<212> TYPE: DNA
<213> ORGANISM: Nannochloropsis oculata

<400> SEQUENCE: 9
gcttctgtgg aagagccagt ggtagtagca gtagcagcag cagtagcagc cgcagcactc       60
agtgttggcg cgagagattg tccatccctt cttaacctac cggaagagaa ataaggcctt      120
tctcccgtag ctgtcttcgt ttgtttgtgc tgattgcttg atatgagagt gttgaattcc      180
tgcatcatgt ttttctctgt agtcctttcc taccccgtc atttctttt ctccctggtt       240 cttcttttgt caccttatt ttacataaaa ttttctttgt ttatagtgag aggaaggtag      300 agagggaaa acaagaacaa cgaacgcaag cgtgtgaaag gagggcgagt agaagagaaa      360
cagatctgtt gagcattgag agtggagccg ggggaaaggc ttgtgtgttg tctttgaaaa      420
agttgtttaa atcacgaatc cgttagttct catgtgtacc tctttcacta catgtgatgg      480 agaaacaaa agtgtgagga ttaattgaag aaaaagaaga gttcgacacg tcaaaccgcc      540
caaaagacgt cacaaagaga acttgattct ctttgccgtg ttgatcctgt cttttccccc      600
agcttttctt gccacccgtg gcacacgaga tggacaagat cag                       643
```

```
<210> SEQ ID NO 10
<211> LENGTH: 32
<212> TYPE: DNA
<213> ORGANISM: Artificial Sequence
<220> FEATURE:
<223> OTHER INFORMATION: Primer No. 10

<400> SEQUENCE: 10
agctgtttcc tgtgtgaaat tgttatccgc tc                                   32
```

```
<210> SEQ ID NO 11
<211> LENGTH: 34
<212> TYPE: DNA
<213> ORGANISM: Artificial Sequence
<220> FEATURE:
<223> OTHER INFORMATION: Primer No. 11

<400> SEQUENCE: 11
ttaagccagc cccgacaccc gccaacaccc gctg                                 34
```

```
<210> SEQ ID NO 12
<211> LENGTH: 34
<212> TYPE: DNA
<213> ORGANISM: Artificial Sequence
<220> FEATURE:
<223> OTHER INFORMATION: Primer No. 12

<400> SEQUENCE: 12
acacaggaaa cagctcctgg gaaatgtgcc attg                                 34
```

```
<210> SEQ ID NO 13
<211> LENGTH: 35
<212> TYPE: DNA
<213> ORGANISM: Artificial Sequence
```

```
<220> FEATURE:
<223> OTHER INFORMATION: Primer No. 13

<400> SEQUENCE: 13
ggacaaaaga ccgccacgtg ttccttctga gaaag                          35

<210> SEQ ID NO 14
<211> LENGTH: 35
<212> TYPE: DNA
<213> ORGANISM: Artificial Sequence
<220> FEATURE:
<223> OTHER INFORMATION: Primer No. 14

<400> SEQUENCE: 14
gatggacaag atcagtttat gtcagacgca aggtc                          35

<210> SEQ ID NO 15
<211> LENGTH: 41
<212> TYPE: DNA
<213> ORGANISM: Artificial Sequence
<220> FEATURE:
<223> OTHER INFORMATION: Primer No. 15

<400> SEQUENCE: 15
tcggggctgg cttaacataa ctggatgaca atgagcacaa g                   41

<210> SEQ ID NO 16
<211> LENGTH: 35
<212> TYPE: DNA
<213> ORGANISM: Artificial Sequence
<220> FEATURE:
<223> OTHER INFORMATION: Primer No. 16

<400> SEQUENCE: 16
acacaggaaa cagctcagta cagacgcgcg agacg                          35

<210> SEQ ID NO 17
<211> LENGTH: 35
<212> TYPE: DNA
<213> ORGANISM: Artificial Sequence
<220> FEATURE:
<223> OTHER INFORMATION: Primer No. 17

<400> SEQUENCE: 17
ggacaaaaga ccgccgattc caaatacgcc agcac                          35

<210> SEQ ID NO 18
<211> LENGTH: 35
<212> TYPE: DNA
<213> ORGANISM: Artificial Sequence
<220> FEATURE:
<223> OTHER INFORMATION: Primer No. 18

<400> SEQUENCE: 18
gatggacaag atcagcatcc atctctatct ttacc                          35

<210> SEQ ID NO 19
<211> LENGTH: 35
<212> TYPE: DNA
<213> ORGANISM: Artificial Sequence
<220> FEATURE:
<223> OTHER INFORMATION: Primer No. 19

<400> SEQUENCE: 19
tcggggctgg cttaacagtc actagcgacg tattc                          35
```

<210> SEQ ID NO 20
<211> LENGTH: 12750
<212> TYPE: DNA
<213> ORGANISM: Nannochloropsis oculata

<400> SEQUENCE: 20
agtaatagaa gaagaagaag aagaaggaat cataaacgta cccattggag gacgacgaca        60
taaagcagca cgaatggcaa atgttcccac gagataaggc caccgaagag acgaccaacc       120
tcctggtaca attgcaggga caggatccgc ttccccgtcc atctaggctg ctgaaacggg       180
cgggccatgg ccaagtgctg gtatttgcgt cgggagaagc ggtggttgtg gcagtggcgt       240
gaagaggagt ggcagggcta tggaagatgg aaggcggcga tgatgatgac gctgccggca       300
agtaaggttg gaaagcggag ctgctaaatg ctgaagccaa cggtgcctgg cagatgactc       360
ctatacctgt ggagcgtata tgtaagtgtg ggtgcctttg aaagggcggt atgttgacag       420
gaggatggga ggccgtcgtc ttctttcctt cgctcttgaa tcaagcgagt gaccgtttcc       480
acgattctat ggggagtcta tgccttgaga atcgggtcca aaattcattt tgggacacaa       540
actagcctcc aaccgggccc aagtagaaaa tatttcatat tcgataagta attgggagtg       600
cattcccggg ttgtggcgtt cataaaaacc ccttttttcct cttttttgaga ctcgccttcc       660 gggcgatcga gctggcagca aacttagaca ctgtccccga gtgattaagg tcgtgtcaat       720
ccccacccct taagacatgt tctacaccat acgacgtgtt gcacctatcg caccaccacc       780
caccaattat caagaccaat gagatcggcg ccaaggacat ctgtgcgccg atgtacgcca       840
gctctattgc gaggtggaga tgcgaaagga ggccatcaga agcagcaaat cgagcgatta       900
caccgaccca gtagatctcg gtataagttg gtggcagaca gtacgcttat tttccccctc       960
agcaaatact cgtccttttt acttcttttt gtttcccacc aatcctgacg tcgtttgttt      1020
cgtcttgcta attgtttcgt cttgctattg agtcataatt agggctgtac aaaaaatcac      1080
taccaaaaaa ggtcgaatag cgcagagtgg aagattgaaa gttttcaag agaagcgaac       1140 gacgacctac tccttccccct cccacgcacc actcttaagt cgtgaaagac aaggaggttt      1200
tatctgacgt tatcttgtcc tcgaggttaa gcttcttcga cacgtcaaca accttcatgc      1260
gacgcatcct catgctccaa tcacatacat acacaaaaca caaaaccacc agaaaccctc      1320
atgtacctct ccctctcccg tttccctccc cccttcctcc ccttactgaa attgtcccga      1380
gctgtcccac ctactggtac taaaagcata acaaatcgtc aatatccaaa cgctcgtaaa      1440
aatccttccc acatacgcct ctcgcggggt gaatctgtcg ttccctaaca ccaacctggc      1500
tgagttgaag gccacttgca acaattctgc cagtccgtta atggttaaaa ttgcctttag      1560
ccgcgtcttg atccgcgaat ttcgtgagaa agactgcacg agagagagga gcacgcctac      1620
caagttcgca cataagagac cgacgacagg taagacgatg agggctcggc ggaaggcacc      1680
agaaatctgg tccgcgagct cgtaaaggtg cgtggcacgt gcagtgagga tcatgaacaa      1740
aatacacaca cccgtgttgc cgactgtacg catgatgcgg gggtagagga tctcgtgacg      1800
ccccgccgag gaggacgttg gttgcgaggt gtagtaccgt tgatagctgt aggaagatga      1860
gacagggccc cacggacggg tcacgggacc cccggcagca gcagctgcgg cgtaattccc      1920
tccttgttgt tgttgtcgct gttgtggctc ttgcggaggg tcgtcgttga cgttgttgcg      1980
tggatgccgg gtgccagatt gttggggagg aggaggtaca aagctgctgc cgccgcgggc      2040
gtcgatgggt ggctgctttt ggtcattcgt gtgagtggta gaggtgcgaa ggagggatga      2100
gtgatggaaa gatacattta gagacatcga gaatgtatgt gtacgtgtaa gttaatgggc      2160

-continued

```
accacaaggg agaacgggta agagagggag gaaacgcgag atggaagaag gcagtcgctc    2220
taacactacc tccacctctc tatcttccgt tctcctggga aatgtgccat tgtaaggagt    2280
atctctgggc tatataactc ttaagtcaca cacattacgc atctcgatat caaacctcca    2340
ttcatccact cctttcctac ccgatgaggc cctctcggaa ggctgcttct gccgcgttgg    2400
ccattgccca gggggcggc actgcctagg ccagaggtag ctgctgctgt cagcatcgta     2460
gcaaggacga gaagggaagg gcccgattga cgtgcttgac ggcgtcgctt gatgccagcc    2520
gcgggagggg atgccatcct tgctgctggt tgtagttgat gatggttcac tttgcggagg    2580
ggataggctg actgtgctct agaatggggt gaatggctag tcgcggtgaa gtggctggtg    2640
gatatgctga tagatggggt tgcgtgggtg tctatgtgtc cgtagacatg taagtcgatg    2700
cagagaaagc gccatcatca caaggaggag gggtcatgcc atgactcgct gatatagcaa    2760
ggggatctat acactagtgt tttgggtccc cttgctgata aagctggtct cgtaattttc    2820
taacgtttcc aagcagccta aattatatcg acaggcctga catagtgctt gttattaagc    2880
gtgctgctcc ctggctagaa aacccgttta cgcctgcaag gcacgtctcg gcttcatgtc    2940
ggggatgtag gcagactgct acagcaccaa acgtgcttta attggtttca acatgtgttg    3000
cttgcatcgc agttaagctg ccggaaggag aggacgggcc aaacaaacaa gcgaagccag    3060
ggcaaacatg ctcttccacc agaccacctg agatggggag tcctcattgg ggcgtcccgc    3120
ctatgtaccg ccgatgatac ggttttgctc aggatgtgca cggttcagac caggaaggaa    3180
acagaacagc aagcgcttgc ccacgagtat ggatggctgg atgaaggctg ggaaagcgcg    3240
caacagattg attgcgagca taacccccaca gcacaccaaa gagcgaatga aaaatggtgc    3300
ttgaattaac tccactcaca caaatataaa atatagactc tatgtacacc tcaagcctct    3360
gcactgttct ttctttatat ttgataacaa aacacgcagg cattcaacac cggcggtttt    3420
gttcagagga gagatcaata atcacgcatc gcaaaatcaa agaaacctta cagcgatgga    3480
aatcgcactg aattgtctgg acttctctct attctgaaga atcacacagc atcttagtca    3540
ccaaccaaca tgcaacaaaa cttatcactc tgtcatgcaa cccgcattct agtccattca    3600
gacacatcta gaccctcgct cctcattatt tatataccat actattatcc tgtcgtcttg    3660
tcatatcagc acagctcaca gcgctcattg caatcaagca ttcctctttt ttctggtaat    3720
atcaccccac caggtcctcc aggctattta tattcatact ctgtttgttt gtcaaaatat    3780
ctctccactg tcccttcgcc tacaaccatc aaccacagtc gtccaaaatc tttctcagaa    3840
ggaacacgtc ctctactcaa aagaggttct agatttaggc ggtgaccttc gctacattcc    3900
ccatctccac cgcatccgcc tcttcagctg cctcgacgga agcgtcactt ctgaccgtgt    3960
cactcagggg gtcgacggca agcaaatcag ggcggaggaa ccagatcgta aaggaaacgg    4020
ccatgacaca ccagcccata attcggaagc cttgggcggt ggaggaaaat ttaccatgca    4080
ggaagaggag ggtgaagatg acggcgccgc aattgccgcc ggcgccgaca atacccgaca    4140
cactgccgcc ttttttgatgg ggcgaggagg gtaggttatg cagaaataga tattttagtg    4200
aatggaatgg tcgctactcc tttcccccc ttcccagttg gtttcctaga tgaagtagat    4260
cccatcctcc cctttcgtc gacctcttct tccctcgctt actcaccggc tgacttggcg    4320 atataggcg taattgcaaa gcacgatccg ttggcagcct gcacaaatat ggaaaaggca    4380
agaaggagga gcgtagcttc ggtctgcgtc ctggcatggg agaaccagat gatgaaaatg    4440
gactcgaaca ggacgagggt gaactgcacg gtcatgcggc ccttaatctc agcgtaggaa    4500
```

-continued

```
ttggcaaggt cgctcagcca tccaccgagc cagcgggcga agatgttggt gatctgtggg   4560
ttgaattagg cagaagtggg tcgaagggct ctgtaaggga ccgtccaatt gtttgttgtt   4620
ttgactaccg gccgcgggac ggagggatgg agggagggaa ggaaagtggg agggtgtttt   4680
acgtaccccg cagagcaagg cgatctgtcc ggccttggtc acatcggcgc cgaactcgtc   4740
gtgaaagtag gaggcggtca tgttgaaaag cacgagttcc accccgaagg tgaccgagta   4800
ctgaaggcac atgatataag acatgtagtt ggatgcagcc gccttgaacg ccgtggtcga   4860
cttgacgggc gactcaccat tcttaataag ctgtctgata tcaccctgtg tagttggtgg   4920
ggaaatggta atccaaattg aggtcagtac tcgcttctgt atgtcttctt cagtcccgtt   4980
cgtctctttt tcctctcctt acctacccga ggggtgtctt gaccaaagaa ttgaacgatg   5040
gcagccgtga taatgagggc aataccaggg aaaacgaagc ttatacgcca ggctttctcc   5100
gggtccacgc cccagctttg gatccctgca aaaatcgaaa ccatgatgac ttgggtgctg   5160
ccacctccga ggttacccca accaccaacg atggcgttgg ctgccccgat gcaccgtttc   5220
ttgaacatgt tggtggtcca cgcctgagac tggacaaatg tagcacccaa aatgcctata   5280
aaaaagcgga gagcgacgag gccctgccag ttgttgacga cgccaatcag gaagacggga   5340
atagcgccga gtgctagtag ccccgccatg gtgaccttgg ggccatagcg gtcgcagagg   5400
gggccgataa ggatacgggt aaagacagtt gaggcgacag cggcaagatt ggacatttga   5460
acttggtcct tagtaagatc taggcttttt tttatgacgg gcataagggg ggcgatggcg   5520
aaccatgcgt tgaaggcctg cggggagcaa aaatgtagag gaaggtgcaa gggaagctga   5580
tgagcgtgct ggtgctgccg tggctgtcgc tggataaatc atccaccccg ttcccccatc   5640
taatccccaa tccccgacct ttgccaacac ttacgatgaa gaagccaaac caggccaggt   5700
gaaaggcgcg catgtgcggg gccgcgaagc tccatatcac gattttgtca gccttctcgg   5760
cctcggtgac ggccgtggtc aggtgcttgg atgactcagg cttggacatg atgcgcagta   5820
tcaggttgta gggcttctgt ttaggatggg gtagcggagg aggggatcgt gcgtgaaggg   5880
cgctgttttc agaggcggag gcggtggcta cacgcccgtc tgaagcacaa gcgaagcact   5940
gctgcgccgg gccgcgcgtg ggcatatttt tatgtcagac gcaaggtctc taaaagtgag   6000
aaagggccgt cattaagtaa gggcgcaaga tcgggcctag ggcacatact ctcccgatat   6060
gtgtaaatgg ccgcttttgt gcctccagca cgcgtgcaaa gtgtcaccaa agcgcacgac   6120
gcaatggcag tagactccag tgaaatgggt aaaagcggca tgtcattagg tgctttggaa   6180
aaaacaatgc caagctttca taaagaagca aacaagcaag acaaatcata ataccccac    6240 tcaagagtaa ctggagatga ccacgttggc taagtccggt tgaaaatcgg cgggtttca    6300 atttatgtcg acatccctgc cccggttcgc gggtcaccat ggaaacatac ttttttttgtt  6360 gcgccacttc tcggccgtac cccacaagac gtatccacga ttgcgaaagg taaagttcta   6420
tttcatgtcc cctggtcgac tggtttgtgt aactccttgc caaaaaccta cctgttactt   6480
tatcaccgac ggcgttggca caacaggcac tgcaccaaaa aaccgccgcc tcgattgggg   6540
gccgcgaaca tgacgtgtcg gaacaggaaa agcaaccgct gcaaggcgcc ggatcttagc   6600
gcgcagtcgt agcagcagga atcgacaata tgtgttctcg tttctgcata cgtcgactct   6660
ggacagctat gactgacccg actctgacca cacttcatga cccacccacc acacaacgag   6720
ggcaggtgcc gcagcagctt tagcacgttg ctcctctaca tggcctttaa actctcacca   6780 caggtgcctca cggcgcctga gccggtccgt gccaccagta cagacgcgcg agacgatgac  6840
acggcagaca agtgggttca gcgcctgcca ggcatgatcc gcctgacggg tcgccacccg   6900
```

-continued

```
tttaacgccg agccgcacac caaggagctg gtcgacgctg gcttcattac ccccgccgcc   6960
atgcactatg tgcggtaagt ccttcttttc tgggtcggcc aatccagttc gtgtctctca   7020
tcatctttct aaactacacc atcacctaca gcaaccacgg cccagtaccc aagcttgcct   7080
gggatgacca ccgcataacc gtgaccggcc ttggcgtagc tgagccccag gttttgtcaa   7140
tggacgaact ggtcgccctg cccaatcgaa ccctgcccgt cactcttgtc tgcgccggca   7200
atcgccgcaa ggaggttaac gtcacccggc agagcaaggg cttcagctgg ggctccggtg   7260
cagtgagcac ctccatttgg acgggcgtgc ccctgcacgt gcttctgcgc cactgtggcg   7320
ttgaccccga tgcgttagag cccggacaat actgggtcaa cttcgacggg cctgacgggg   7380
agctgcccaa gggcatttat ggcacgagta tccccctcct caaggtaagc attcgggcat   7440
atatttatgc atgcttgtgc tcattgtcat ccagttatga caaaactatc catcttttct   7500
tttttccagg cgctggatcc agcacaggat gtgcttgtgg ccttcaagca gaaccacgag   7560
cgcctcctcc ccgaccacgg cttccctgtc cgcctcatta ttccaggtac acaatcaaac   7620
atacacatac acacccatac acgcacatac atacatgaac cacagccata ttactcactt   7680
tcctttttat ctcctctact tgcagggtac atagggggac ggatgatcaa atggcttact   7740
cgcatcacta tcagccgcca agagtcgcag tccttttacc acttccacga caatcgcgtc   7800
ctgccctcgt cggtggacca agagcgcgcg gataatgagg gctggtggcg caagcctgag   7860
tacatcatca acgacctcaa ccttaactcg gccatcaccc atccggtacg tactcgtgtc   7920
cgcgggcctc agctgggatt acgaaagttt acaaacgtgc aagctcgccg cttatactgc   7980
tgttcgtcat tttccctgcc agactcacga cgaggagatc ccgctgaaga aaggcactta   8040
caaactccaa ggctacgcct actgtggtgg cggccggcaa gtgcaacgca tggaggtctc   8100
cctcgacgat ggcaaggtag gaagtatcac cttgtcgcgg ttttcacact gctatcattg   8160
actcaatcga catttacaca cccattccga ctacgcacca cgagtagagc tgggaactag   8220
ctcagctgag cagtgaggag tacccaactg aacacggccg cttctggtgc tggcgtattt   8280
ggaatcttga tgtcgacatc ctacgtctgg tgagtgcagc ttgagaacga gcgagaaacg   8340
tctgtgttcc atcacgctct catatataca atccctccct ctctcatagg tgggctgtac   8400
gaatgtcgcc tgtcgtgcat gggacaactc gcagaacaca cagcctcgag acttgacgtg   8460
gaacgtccta ggcagtgagt atttcgtttc ctctcttcta gagatacttt tattccatcc   8520
atctctatct ttacctgtgt ctatgagagt aagagtaatc gtcacacctt attcataccc   8580
ctgaactccc ctttccaccc ctcccttccc tacccacagt gatgaacaac agctggttcc   8640
ggcttacaac cgcggttagt ctcaacgatc gccagcagcc tgtcgtccgc atcaagcacc   8700
cggcgcccat tgctcctggt gggtggatgg aggcaggggc cgacgagact gtaaatgtac   8760
aggccaagac aacgggtacc ggtagcggac ggtcacacgt ggaagacaag tctgtcccat   8820
cgatagcgca gcgtaaggat ttgtccgtca tcacgcgcga agagttggcg cggcacaaca   8880
gcaagtacgt gcggggggaa gagggcatga ggaaggtggg tggagggagg gcaacgacga   8940
tgtttgtcca tcaatacgtg tatatgacgc acagtcaacc gctgactaaa cctactgcac   9000
gaaaatcaca gaactgactg ctggatcgct gtcaagggtc aggtctacga tgtgaccccc   9060
tacttgcagg agcacccggg cggcgtggcc gccatcgtca tgaacgccgg caaagacgcc   9120
accgaggatt ttgaggtacg caacatatga atatgcaagc ccgccccgca tgcatcgatg   9180
agagcacggc acttaattgt gcccaccaac cacatacaca cgcaggcgat ccactccaaa   9240
```

-continued

```
agggcctggg ctatgctgga tgagtatctg gtcggcaccc tcggggcttc tttgacctcc      9300
tcctcccctg aagcctccgc catcgccgcg cccaaggagg ctgccgtggc gctgcaaggc      9360
aagaaccgcg ccatcaagtg caagctcgtg ttcaaggagt acgagagtcc cgacgtcctg      9420
cgtatccgat ttggcctccc gcagccagac cagcccctgg gcctccctgt tgggatgcat      9480
atcggcctgc gcgccgtgat caacggtgag agtaccaagc ggcaatacac gcccgtgtcg      9540
gacggggacg ccaagggtca cgtggagctg ctggtcaagg tacgtgcgtg caggcaaatg      9600
ggttttgagt gattggacga tggagcctct ctcatcctct gcgcgagcta ggaccatctg      9660
acattgccag tccccgtcgc cccttgcgga cctgtagacc ccgtagcccc ccttgcacgc      9720
acagcgcctt atttcttgac acacatgcac accctaccac acaggtctac cgcgccaacc      9780
agcacccgcg ctttcccgac ggcgggctta tgtcgcagca cctagaccgt atgtccctcg      9840
gcgactgcat agatattgac ggacccctcg gtcacattac ttacgagggc cccggctgca      9900
ttcgccaact gggggaggac gtgcatgtca agcactttgt ggcggtcgcc ggcggcacgg      9960
gcatcacgcc agtcgtgcag gtacgttgac aatcgacgtc ataaattttg aggaaaaaag     10020
gtgttggtgt cgggaatacg tcgctagtga ctgattcgaa tccactcaat caactctcac     10080
cgcaggtgct tcgtgccgtg ttagagaatc cttgcgacac tacccgcttt tccctcatct     10140
atgcggcccg ggttccagag gatttgctcc tgcgcgagga gctggacgcc tgggcggagc     10200
agtacgaaca gtttacggta aggaatagtg ttctcgacat ttggtctcag cttccgctca     10260
ttttcttctt gacacgactc actaactcaa cattctgctt tacttatctc ttaatttaag     10320
gtgcactaca ccgtcgatgt tcctccccct gattggccgt actccgtcgg tttcctcacg     10380
gccgagatgc tggcggcgaa tttccccgag gccaccaagg acatgggcgc gcttatctgc     10440 ggcccgcgc cgatggtgaa cttcgccgtg aaacccaacc tagaaaagct tggttacacc     10500
gaggaccagt ttttcatctt ttaaatgaat gtgggtgcat gcgtgtatgc gtgcatgtat     10560
gcgtgtatgc aagtgcgggc gtgcgcgtat gcgagtggat gcgtagtgta ccagggttga     10620
cctgagcaag ctagatgtgc tgaacccgcg ggggggggtg tatgcagaga gcgaaagcaa     10680
ttttgagtct gaaggagaga atggaccgct ataacagggc ttgtacattt aggaattata     10740
tatatacata tatgatttgt atggtggaaa cgatgattta ccaggatgtt gtcctggtaa     10800
tctggagtag tgagatgggt gaagcgcgac cttgtggatc tacttaactt tttcatcata     10860
cacgactagt accttaggca gcttagtcag aaaaatgcag aaagaataaa aacgtggaaa     10920
cggagtgtga tgggtcggaa tgttgatttg tgtgattttt ttttttataca acctgggcct     10980 ctcccataaa tctcacgggg gtgctgctgc tttttttacc actcttgctg ctgcttctgc     11040
ttcttgccca gcgggccaaa gcctccgcgc tggctaccat ccacccgtga tatttccaat     11100
tgtaaggaag ataatggagg acgggtaaag cagtccacgt ccacatggtg gcgccttaga     11160
catggcagaa aagaggcctg atcgaggaga gtgcaccctg gagggagggt gactgagtga     11220
tgaacagcct cccgcgaacc ttccttcact catcctccat catgccagcg cttgcgtacc     11280
gctctggctg gagatttgcc tctcagattg cacaaggcaa cgagttattt ccttcatctt     11340
catataaccc tcctccctcc cgccctcccg gaagccgggt tgacggggc cgcgctgtta     11400 aggcctgtga tgactgctct tgttcccaat actacaactg tgaggataag caggaaagtg     11460
ttatgtcgac gcacttgccc aggacaaaat tgcttgaggc cttccgcgag agggagcgag     11520
gtcatccttg caattgatca tgacgtatgg agatgggagg cttgctgcta cagtagtggc     11580
tactgctgcg gatcatgagg ttgaaggctg aaatggtgtg cgaggtagca agaaggatgg     11640
```

```
tttgagggta taggaacgct ggtggagagc aaggaaagtg cctgagaggc gacatcacca   11700
taacgccgcc ccgcttcgtc gcagtctaac ccaatcctat cgcactttgt ttcaatgaac   11760
aaggtcttct tgaccatgtt ttcagatctc cttaaattgt accgattgtc cagcgtgctg   11820
ctgggggcct tggatcagca ggcccgtgac agagcaggca cgtgcaagta tctgattacg   11880
tccctcctcc ccgttcccaa caagaaaaag caggatgctg cagcaaatca acaagacttt   11940
ggagccactc ttgggcgagc acaatgttgc ggcagcggta cgtgcgtgtc atcttacctg   12000
atctctacat tcacagtttc tctggttcct gcctgatcag tgcacctgag ggattcatgt   12060
gcagcgtttc ttttgtgtga taccttgaac attttttttg gtgccggtac atgcttgtgc   12120
tgatggccac gagctctcac tggagttgtt gttcggatgg gagcttgcgc ttgtgtatat   12180
gcatgtctcc atggtatgtg ttcttccctg tgtgccttcc ccacttacgt gtctacttct   12240
caattttttt ttgtaatagg tgacgctgag tgtaattgcc ttgaccattg tcgtttccg    12300 cgttcgacga ccatgctcct tcgacgtgat gaacatcatg aagaacagcg acttcgaggc   12360
gcataaagcc aaggtaggtg tcgggttggg aggacgagag gacgggaggc gttgaacaat   12420
ggggtgttaa gctaggggac aagccatact tatgtgacat gaaagctgcc tttcgcaagc   12480
gtttgacctc tccatgtttc catgggataa gaacaacctt ttcattatat ctatttctcc   12540
tcttcttcca tcaggacgtg caaacctcag tggatcagta cgctaccctt ttcaccggcg   12600
cccggaccaa aatcggctcc atctccagcg ccggcagtat cgagtcccgg caacaaaact   12660
acaaaacatt ggtgggaaac ttctacgatc tagccaccga cttttacgag tacggctggg   12720
gtcaggtacg gagggagtga gtgagggagg                                    12750

<210> SEQ ID NO 21
<211> LENGTH: 1596
<212> TYPE: DNA
<213> ORGANISM: Nannochloropsis oculata

<400> SEQUENCE: 21
acgtgttcct tctgagaaag attttggacg actgtggttg atggttgtag gcgaagggac     60
agtggagaga tattttgaca aacaaacaga gtatgaatat aaatagcctg gaggacctgg    120
tggggtgata ttaccagaaa aaagaggaat gcttgattgc aatgagcgct gtgagctgtg    180
ctgatatgac aagacgacag gataaatagta tggtatataa ataatgagga gcgagggtct    240
agatgtgtct gaatggacta gaatgcgggt tgcatgacag agtgataagt tttgttgcat    300
gttggttggt gactaagatg ctgtgtgatt cttcagaata gagagaagtc cagacaattc    360
agtgcgattt ccatcgctgt aaggtttctt tgattttgcg atgcgtgatt attgatctct    420
cctctgaaca aaaccgccgg tgttgaatgc ctgcgtgttt tgttatcaaa tataaagaaa    480
gaacagtgca gaggcttgag gtgtacatag agtctatatt ttatatttgt gtgagtggag    540
ttaattcaag caccattttt cattcgctct ttggtgtgct gtggggttat gctcgcaatc    600
aatctgttgc gcgctttccc agccttcatc cagccatcca tactcgtggg caagcgcttg    660
ctgttctgtt tccttcctgg tctgaaccgt gcacatcctg agcaaaaccg tatcatcggc    720
ggtacatagg cgggacgccc caatgaggac tccccatctc aggtggtctg gtggaagagc    780
atgtttgccc tggcttcgct tgtttgtttg gcccgtcctc tccttccggc agcttaactg    840
cgatgcaagc aacacatgtt gaaaccaatt aaagcacgtt tggtgctgta gcagtctgcc    900
tacatccccg acatgaagcc gagacgtgcc ttgcaggcgt aaacgggttt tctagccagg    960
```

-continued

```
gagcagcacg cttaataaca agcactatgt caggcctgtc gatataattt aggctgcttg      1020
gaaacgttag aaaattacga gaccagcttt atcagcaagg ggacccaaaa cactagtgta      1080
tagatcccct tgctatatca gcgagtcatg gcatgacccc tcctccttgt gatgatggcg      1140
ctttctctgc atcgacttac atgtctacgg acacatagac acccacgcaa ccccatctat      1200
cagcatatcc accagccact tcaccgcgac tagccattca ccccattcta gagcacagtc      1260
agcctatccc ctccgcaaag tgaaccatca tcaactacaa ccagcagcaa ggatggcatc      1320
ccctcccgcg gctggcatca agcgacgccg tcaagcacgt caatcgggcc cttcccttct      1380
cgtccttgct acgatgctga cagcagcagc tacctctggc ctaggcagtg ccgcccccct      1440
gggcaatggc caacgcggca gaagcagcct tccgagaggg cctcatcggg taggaaagga      1500
gtggatgaat ggaggtttga tatcgagatg cgtaatgtgt gtgacttaag agttatatag      1560
cccagagata ctccttacaa tggcacattt cccagg                                1596
```

```
<210> SEQ ID NO 22
<211> LENGTH: 1511
<212> TYPE: DNA
<213> ORGANISM: Nannochloropsis oculata

<400> SEQUENCE: 22
```

```
cataactgga tgacaatgag cacaagcatg cataaatata tgcccgaatg cttaccttga        60 ggaggggat actcgtgcca taaatgccct tgggcagctc cccgtcaggc ccgtcgaagt       120
tgacccagta ttgtccgggc tctaacgcat cggggtcaac gccacagtgg cgcagaagca       180
cgtgcagggg cacgcccgtc caaatggagg tgctcactgc accggagccc cagctgaagc       240
ccttgctctg ccgggtgacg ttaacctcct tgcggcgatt gccggcgcag acaagagtga       300
cgggcagggt tcgattgggc agggcgacca gttcgtccat tgacaaaacc tggggctcag       360
ctacgccaag gccggtcacg gttatgcggt ggtcatccca ggcaagcttg ggtactgggc       420
cgtggttgct gtaggtgatg gtgtagttta gaaagatgat gagagacacg aactggattg       480
gccgacccag aaaagaagga cttaccgcac atagtgcatg gcggcggggg taatgaagcc       540
agcgtcgacc agctccttgg tgtgcggctc ggcgttaaac gggtggcgac ccgtcaggcg       600
gatcatgcct ggcaggcgct gaacccactt gtctgccgtg tcatcgtctc gcgcgtctgt       660
actggtggca cggaccggct caggcgccgt aggcacctgt ggtgagagtt taaaggccat       720
gtagaggagc aacgtgctaa agctgctgcg gcacctgccc tcgttgtgtg gtgggtgggt       780
catgaagtgt ggtcagagtc gggtcagtca tagctgtcca gagtcgacgt atgcagaaac       840
gagaacacat attgtcgatt cctgctgcta cgactgcgcg ctaagatccg gcgccttgca       900
gcggttgctt ttcctgttcc gacacgtcat gttcgcggcc cccaatcgag gcggcggttt       960
tttggtgcag tgcctgttgt gccaacgccg tcggtgataa agtaacaggt aggtttttgg      1020
caaggagtta cacaaaccag tcgaccaggg gacatgaaat agaactttac ctttcgcaat      1080
cgtggatacg tcttgtgggg tacggccgag aagtggcgca acaaaaaaag tatgtttcca      1140
tggtgacccg cgaaccgggg cagggatgtc gacataaatt gaaaaccgc cgattttcaa       1200 ccggacttag ccaacgtggt catctccagt tactcttgag tgggggtatt atgatttgtc      1260
ttgcttgttt gcttctttat gaaagcttgg cattgttttt tccaaagcac ctaatgacat      1320 gccgcttta cccatttcac tggagtctac tgccattgcg tcgtgcgctt tggtgacact       1380
ttgcacgcgt gctggaggca caaaagcggc catttacaca tatcgggaga gtatgtgccc      1440
taggcccgat cttgcgccct tacttaatga cggcccttc tcacttttag agaccttgcg      1500
```

```
tctgacataa a                                                         1511

<210> SEQ ID NO 23
<211> LENGTH: 1471
<212> TYPE: DNA
<213> ORGANISM: Nannochloropsis oculata

<400> SEQUENCE: 23
cagtacagac gcgcgagacg atgacacggc agacaagtgg gttcagcgcc tgccaggcat       60
gatccgcctg acgggtcgcc acccgtttaa cgccgagccg cacaccaagg agctggtcga      120
cgctggcttc attaccccccg ccgccatgca ctatgtgcgg taagtccttc ttttctgggt      180
cggccaatcc agttcgtgtc tctcatcatc tttctaaact acaccatcac ctacagcaac      240
cacggcccag tacccaagct tgcctgggat gaccaccgca taaccgtgac cggccttggc      300
gtagctgagc cccaggtttt gtcaatggac gaactggtcg ccctgcccaa tcgaaccctg      360
cccgtcactc ttgtctgcgc cggcaatcgc cgcaaggagg ttaacgtcac ccggcagagc      420
aagggcttca gctggggctc cggtgcagtg agcacctcca tttggacggg cgtgcccctg      480
cacgtgcttc tgcgccactg tggcgttgac cccgatgcgt tagagcccgg acaatactgg      540
gtcaacttcg acgggcctga cggggagctg cccaagggca tttatggcac gagtatcccc      600
ctcctcaagg taagcattcg ggcatatatt tatgcatgct tgtgctcatt gtcatccagt      660
tatgacaaaa ctatccatct tttctttttt ccaggcgctg gatccagcac aggatgtgct      720
tgtggccttc aagcagaacc acgagcgcct cctccccgac cacggcttcc ctgtccgcct      780
cattattcca ggtacacaat caaacataca catacacacc catacacgca catacataca      840
tgaaccacag ccatattact cactttcctt tttatctcct ctacttgcag ggtacatagg      900
gggacggatg atcaaatggc ttactcgcat cactatcagc cgccaagagt cgcagtcctt      960
ttaccacttc cacgacaatc gcgtcctgcc ctcgtcggtg gaccaagagc gcgcggataa     1020
tgagggctgg tggcgcaagc ctgagtacat catcaacgac ctcaacctta actcggccat     1080
cacccatccg gtacgtactc gtgtccgcgg gcctcagctg ggattacgaa agtttacaaa     1140
cgtgcaagct cgccgcttat actgctgttc gtcattttcc ctgccagact cacgacgagg     1200
agatcccgct gaagaaaggc acttacaaac tccaaggcta cgcctactgt ggtggcggcc     1260
ggcaagtgca acgcatggag gtctccctcg acgatggcaa ggtaggaagt atcaccttgt     1320
cgcggttttc acactgctat cattgactca atcgacattt acacacccat tccgactacg     1380
caccacgagt agagctggga actagctcag ctgagcagtg aggagtaccc aactgaacac     1440
ggccgcttct ggtgctggcg tatttggaat c                                   1471

<210> SEQ ID NO 24
<211> LENGTH: 1538
<212> TYPE: DNA
<213> ORGANISM: Nannochloropsis oculata

<400> SEQUENCE: 24
catccatctc tatctttacc tgtgtctatg agagtaagag taatcgtcac accttattca       60 taccccctgaa ctcccctttc cacccctccc ttccctaccc acagtgatga acaacagctg      120
gttccggctt acaaccgcgg ttagtctcaa cgatcgccag cagcctgtcg tccgcatcaa      180
gcacccggcg cccattgctc ctggtgggtg gatggaggcg ggggccgacg agactgtaaa      240
tgtacaggcc aagacaacgg gtaccggtag cggacggtca cacgtggaag acaagtctgt      300
```

```
cccatcgata gcgcagcgta aggatttgtc cgtcatcacg cgcgaagagt tggcgcggca      360
caacagcaag tacgtgcggg gggaagaggg catgaggaag gtgggtggag ggagggcaac      420
gacgatgttt gtccatcaat acgtgtatat gacgcacagt caaccgctga ctaaacctac      480
tgcacgaaaa tcacagaact gactgctgga tcgctgtcaa gggtcaggtc tacgatgtga      540 cccctactt gcaggagcac ccgggcggcg tggccgccat cgtcatgaac gccggcaaag       600
acgccaccga ggattttgag gtacgcaaca tatgaatatg caagcccgcc ccgcatgcat      660
cgatgagagc acggcactta attgtgccca ccaaccacat acacacgcag gcgatccact      720
ccaaaagggc ctgggctatg ctggatgagt atctggtcgg caccctcggg gcttcttttga     780 cctcctcctc ccctgaagcc tccgccatcg ccgcgcccaa ggaggctgcc gtggcgctgc      840
aaggcaagaa ccgcgccatc aagtgcaagc tcgtgttcaa ggagtacgag agtcccgacg      900
tcctgcgtat ccgatttggc ctcccgcagc cagaccagcc cctgggcctc cctgttggga      960
tgcatatcgg cctgcgcgcc gtgatcaacg gtgagagtac caagcggcaa tacacgcccg     1020
tgtcggacgg ggacgccaag ggtcacgtgg agctgctggt caaggtacgt gcgtgcaggc     1080
aaatgggttt tgagtgattg gacgatggag cctctctcat cctctgcgcg agctaggacc     1140
atctgacatt gccagtcccc gtcgcccctt gcggacctgt agaccccgta gcccccttg      1200 cacgcacagc gccttatttc ttgacacaca tgcacaccct accacacagg tctaccgcgc     1260
caaccagcac ccgcgctttc ccgacggcgg gcttatgtcg cagcacctag accgtatgtc     1320
cctcggcgac tgcatagata ttgacggacc cctcggtcac attacttacg agggccccgg     1380
ctgcattcgc caactggggg aggacgtgca tgtcaagac tttgtggcgg tcgccggcgg       1440
cacgggcatc acgccagtcg tgcaggtacg ttgacaatcg acgtcataaa ttttgaggaa     1500
aaaaggtgtt ggtgtcggga atacgtcgct agtgactg                            1538
```

```
<210> SEQ ID NO 25
<211> LENGTH: 32
<212> TYPE: DNA
<213> ORGANISM: Artificial Sequence
<220> FEATURE:
<223> OTHER INFORMATION: Primer No. 25

<400> SEQUENCE: 25
ggcggtcttt tgtcctttcc tctatagccc gc                                     32

<210> SEQ ID NO 26
<211> LENGTH: 34
<212> TYPE: DNA
<213> ORGANISM: Artificial Sequence
<220> FEATURE:
<223> OTHER INFORMATION: Primer No. 26

<400> SEQUENCE: 26
ctgatcttgt ccatctcgtg tgccacgggt ggca                                   34

<210> SEQ ID NO 27
<211> LENGTH: 26
<212> TYPE: DNA
<213> ORGANISM: Artificial Sequence
<220> FEATURE:
<223> OTHER INFORMATION: Primer No. 27

<400> SEQUENCE: 27
cctgggaaat gtgccattgt aaggag                                            26
```

<210> SEQ ID NO 28
<211> LENGTH: 26
<212> TYPE: DNA
<213> ORGANISM: Artificial Sequence
<220> FEATURE:
<223> OTHER INFORMATION: Primer No. 28

<400> SEQUENCE: 28
cataactgga tgacaatgag cacaag                                                 26

<210> SEQ ID NO 29
<211> LENGTH: 20
<212> TYPE: DNA
<213> ORGANISM: Artificial Sequence
<220> FEATURE:
<223> OTHER INFORMATION: Primer No. 29

<400> SEQUENCE: 29
cagtacagac gcgcgagacg                                                        20

<210> SEQ ID NO 30
<211> LENGTH: 20
<212> TYPE: DNA
<213> ORGANISM: Artificial Sequence
<220> FEATURE:
<223> OTHER INFORMATION: Primer No. 30

<400> SEQUENCE: 30
cagtcactag cgacgtattc                                                        20

<210> SEQ ID NO 31
<211> LENGTH: 25
<212> TYPE: DNA
<213> ORGANISM: Artificial Sequence
<220> FEATURE:
<223> OTHER INFORMATION: Primer No. 31

<400> SEQUENCE: 31
gtgccgcagc agctttagca cgttg                                                  25

<210> SEQ ID NO 32
<211> LENGTH: 25
<212> TYPE: DNA
<213> ORGANISM: Artificial Sequence
<220> FEATURE:
<223> OTHER INFORMATION: Primer No. 32

<400> SEQUENCE: 32
agtgtcgcaa ggattctcta acacg                                                  25

<210> SEQ ID NO 33
<211> LENGTH: 20
<212> TYPE: DNA
<213> ORGANISM: Artificial Sequence
<220> FEATURE:
<223> OTHER INFORMATION: Primer No. 33

<400> SEQUENCE: 33
gacgtgaccc tgttcatcag                                                        20

<210> SEQ ID NO 34
<211> LENGTH: 20
<212> TYPE: DNA
<213> ORGANISM: Artificial Sequence
<220> FEATURE:
<223> OTHER INFORMATION: Primer No. 34

<400> SEQUENCE: 34
tgcacgacag gcgacattcg                                                    20

<210> SEQ ID NO 35
<211> LENGTH: 27
<212> TYPE: DNA
<213> ORGANISM: Artificial Sequence
<220> FEATURE:
<223> OTHER INFORMATION: Primer No. 35

<400> SEQUENCE: 35
gcacagctca cagcgctcat tgcaatc                                            27

<210> SEQ ID NO 36
<211> LENGTH: 33
<212> TYPE: DNA
<213> ORGANISM: Artificial Sequence
<220> FEATURE:
<223> OTHER INFORMATION: Primer No. 36

<400> SEQUENCE: 36
ttaaaagatg aaaaactggt cctcggtgta acc                                     33

<210> SEQ ID NO 37
<211> LENGTH: 35
<212> TYPE: DNA
<213> ORGANISM: Artificial Sequence
<220> FEATURE:
<223> OTHER INFORMATION: Primer No. 37

<400> SEQUENCE: 37
agatagagat ggatgacgtg ttccttctga gaaag                                   35

<210> SEQ ID NO 38
<211> LENGTH: 30
<212> TYPE: DNA
<213> ORGANISM: Artificial Sequence
<220> FEATURE:
<223> OTHER INFORMATION: Primer No. 38

<400> SEQUENCE: 38
catccatctc tatctttacc tgtgtctatg                                         30

<210> SEQ ID NO 39
<211> LENGTH: 1407
<212> TYPE: DNA
<213> ORGANISM: Nannochloropsis oculata

<400> SEQUENCE: 39
atgtccaagc ctgagtcatc caagcacctg accacggccg tcaccgaggc cgagaaggct        60
gacaaaatcg tgatatggag cttcgcggcc ccgcacatgc gcgcctttca cctggcctgg       120
tttggcttct tcatcgcctt caacgcatgg ttcgccatcg cccccttat gcccgtcata        180 aaaaaaagcc tagatcttac taaggaccaa gttcaaatgt ccaatcttgc cgctgtcgcc       240
tcaactgtct ttacccgtat ccttatcggc cccctctgcg accgctatgg ccccaaggtc       300
accatggcgg ggctactagc actcggcgct attcccgtct tcctgattgg cgtcgtcaac       360
aactggcagg gcctcgtcgc tctccgcttt tttataggca ttttgggtgc tacatttgtc       420
cagtctcagg cgtggaccac caacatgttc aagaaacggt gcatcggggc agccaacgcc       480
atcgttggtg gttggggtaa cctcggaggt ggcagcaccc aagtcatcat ggtttcgatt       540
tttgcaggga tccaaagctg gggcgtggac ccggagaaag cctggcgtat aagcttcgtt       600

-continued

```
ttccctggta ttgccctcat tatcacggct gccatcgttc aattctttgg tcaagacacc      660
cctcggggtg atatcagaca gcttattaag aatggtgagt cgcccgtcaa gtcgaccacg      720
gcgttcaagg cggctgcatc caactacatg tcttatatca tgtgccttca gtactcggtc      780
accttcgggg tggaactcgt gcttttcaac atgaccgcct cctactttca cgacgagttc      840
ggcgccgatg tgaccaaggc cggacagatc gccttgctct gcgggatcac caacatcttc      900
gcccgctggc tcggtggatg gctgagcgac cttgccaatt cctacgctga gattaagggc      960
cgcatgaccg tgcagttcac cctcgtcctg ttcgagtcca ttttcatcat ctggttctcc     1020
catgccagga cgcagaccga agctacgctc ctccttcttg cctttccat atttgtgcag     1080 gctgccaacg gatcgtgctt tgcaattacg ccctatatcg ccaagtcagc cggcggcagt     1140
gtgtcgggta ttgtcggcgc cggcggcaat tgcggcgccg tcatcttcac cctcctcttc     1200
ctgcatggta aattttcctc caccgcccaa ggcttccgaa ttatgggctg gtgtgtcatg     1260
gccgtttcct ttacgatctg gttcctccgc cctgatttgc ttgccgtcga cccccctgagt     1320 gacacggtca gaagtgacgc ttccgtcgag gcagctgaag aggcggatgc ggtggagatg     1380
gggaatgtag cgaaggtcac cgcctaa                                         1407
```

<210> SEQ ID NO 40
<211> LENGTH: 2544
<212> TYPE: DNA
<213> ORGANISM: Nannochloropsis oculata

<400> SEQUENCE: 40

```
atgacccacc caccacacaa cgagggcagg tgccgcagca gctttagcac gttgctcctc       60
tacatggcct ttaaactctc accacaggtg cctacggcgc ctgagccggt ccgtgccacc      120
agtacagacg cgcgagacga tgacacggca gacaagtggg ttcagcgcct gccaggcatg      180
atccgcctga cgggtcgcca cccgtttaac gccgagccgc acaccaagga gctggtcgac      240
gctggcttca ttaccccgc cgccatgcac tatgtgcgca accacggccc agtacccaag      300
cttgcctggg atgaccaccg cataaccgtg accggccttg cgtagctga gccccaggtt      360 ttgtcaatgg acgaactggt cgccctgccc aatcgaaccc tgcccgtcac tcttgtctgc      420
gccggcaatc gccgcaagga ggttaacgtc acccggcaga gcaagggctt cagctggggc      480
tccggtgcag tgagcacctc catttggacg ggcgtgcccc tgcacgtgct tctgcgccac      540
tgtggcgttg accccgatgc gttagagccc ggacaatact gggtcaactt cgacgggcct      600
gacggggagc tgcccaaggg catttatggc acgagtatcc ccctcctcaa ggcgctggat      660
ccagcacagg atgtgcttgt ggccttcaag cagaaccacg agcgcctcct ccccgaccac      720
ggcttccctg tccgcctcat tattccaggg tacatagggg gacggatgat caaatggctt      780
actcgcatca ctatcagccg ccaagagtcg cagtcctttt accacttcca cgacaatcgc      840
gtcctgccct cgtcggtgga ccaagagcgc gcggataatg agggctggtg gcgcaagcct      900
gagtacatca tcaacgacct caaccttaac tcggccatca cccatccgac tcacgacgag      960
gagatcccgc tgaagaaagg cacttacaaa ctccaaggct acgcctactg tggtggcggc     1020
cggcaagtgc aacgcatgga ggtctccctc gacgatggca gagagctggga actagctcag     1080 ctgagcagtg aggagtaccc aactgaacac ggccgcttct ggtgctggcg tatttggaat     1140
cttgatgtcg acatcctacg tctggtgggc tgtacgaatg tcgcctgtcg tgcatgggac     1200
aactcgcaga acacacagcc tcgagacttg acgtggaacg tcctaggcat gatgaacaac     1260
```

-continued

```
agctggttcc ggcttacaac cgcggttagt ctcaacgatc gccagcagcc tgtcgtccgc    1320
atcaagcacc cggcgcccat tgctcctggt gggtggatgg aggcaggggc cgacgagact    1380
gtaaatgtac aggccaagac aacgggtacc ggtagcggac ggtcacacgt ggaagacaag    1440
tctgtcccat cgatagcgca gcgtaaggat ttgtccgtca tcacgcgcga agagttggcg    1500
cggcacaaca gcaaaactga ctgctggatc gctgtcaagg gtcaggtcta cgatgtgacc    1560
ccctacttgc aggagcaccc gggcggcgtg gccgccatcg tcatgaacgc cggcaaagac    1620
gccaccgagg attttgaggc gatccactcc aaaagggcct gggctatgct ggatgagtat    1680
ctggtcggca ccctcggggc ttctttgacc tcctcctccc ctgaagcctc cgccatcgcc    1740
gcgcccaagg aggctgccgt ggcgctgcaa ggcaagaacc gcgccatcaa gtgcaagctc    1800
gtgttcaagg agtacgagag tcccgacgtc ctgcgtatcc gatttggcct cccgcagcca    1860
gaccagcccc tgggcctccc tgttgggatg catatcggcc tgcgcgccgt gatcaacggt    1920
gagagtacca gcggcaata cacgcccgtg tcggacgggg acgccaaggg tcacgtggag    1980
ctgctggtca aggtctaccg cgccaaccag caccgcgcgt ttcccgacgg cgggcttatg    2040
tcgcagcacc tagaccgtat gtccctcggc gactgcatag atattgacgg acccctcggt    2100
cacattactt acgagggccc cggctgcatt cgccaactgg gggaggacgt gcatgtcaag    2160
cactttgtgg cggtcgccgg cggcacgggc atcacgccag tcgtgcaggt gcttcgtgcc    2220
gtgttagaga atccttgcga cactacccgc ttttccctca tctatgcggc ccgggttcca    2280
gaggatttgc tcctgcgcga ggagctggac gcctgggcgg agcagtacga acagtttacg    2340
gtgcactaca ccgtcgatgt tcctccccct gattggccgt actccgtcgg tttcctcacg    2400
gccgagatgc tggcggcgaa tttccccgag gccaccaagg acatgggcgc gcttatctgc    2460
ggcccgccgc cgatggtgaa cttcgccgtg aaacccaacc tagaaaagct tggttacacc    2520
gaggaccagt ttttcatctt ttaa                                           2544
```

```
<210> SEQ ID NO 41
<211> LENGTH: 468
<212> TYPE: PRT
<213> ORGANISM: Nannochloropsis oculata

<400> SEQUENCE: 41

Met Ser Lys Pro Glu Ser Ser Lys His Leu Thr Thr Ala Val Thr Glu
1               5                   10                  15

Ala Glu Lys Ala Asp Lys Ile Val Ile Trp Ser Phe Ala Ala Pro His
            20                  25                  30

Met Arg Ala Phe His Leu Ala Trp Phe Gly Phe Phe Ile Ala Phe Asn
        35                  40                  45

Ala Trp Phe Ala Ile Ala Pro Leu Met Pro Val Ile Lys Lys Ser Leu
    50                  55                  60

Asp Leu Thr Lys Asp Gln Val Gln Met Ser Asn Leu Ala Ala Val Ala
65                  70                  75                  80

Ser Thr Val Phe Thr Arg Ile Leu Ile Gly Pro Leu Cys Asp Arg Tyr
                85                  90                  95

Gly Pro Lys Val Thr Met Ala Gly Leu Leu Ala Leu Gly Ala Ile Pro
            100                 105                 110

Val Phe Leu Ile Gly Val Val Asn Asn Trp Gln Gly Leu Val Ala Leu
        115                 120                 125

Arg Phe Phe Ile Gly Ile Leu Gly Ala Thr Phe Val Gln Ser Gln Ala
    130                 135                 140
```

```
Trp Thr Thr Asn Met Phe Lys Lys Arg Cys Ile Gly Ala Ala Asn Ala
145                 150                 155                 160

Ile Val Gly Gly Trp Gly Asn Leu Gly Gly Gly Ser Thr Gln Val Ile
                165                 170                 175

Met Val Ser Ile Phe Ala Gly Ile Gln Ser Trp Gly Val Asp Pro Glu
                180                 185                 190

Lys Ala Trp Arg Ile Ser Phe Val Phe Pro Gly Ile Ala Leu Ile Ile
                195                 200                 205

Thr Ala Ala Ile Val Gln Phe Phe Gly Gln Asp Thr Pro Arg Gly Asp
        210                 215                 220

Ile Arg Gln Leu Ile Lys Asn Gly Glu Ser Pro Val Lys Ser Thr Thr
225                 230                 235                 240

Ala Phe Lys Ala Ala Ala Ser Asn Tyr Met Ser Tyr Ile Met Cys Leu
                245                 250                 255

Gln Tyr Ser Val Thr Phe Gly Val Glu Leu Val Leu Phe Asn Met Thr
                260                 265                 270

Ala Ser Tyr Phe His Asp Glu Phe Gly Ala Asp Val Thr Lys Ala Gly
                275                 280                 285

Gln Ile Ala Leu Leu Cys Gly Ile Thr Asn Ile Phe Ala Arg Trp Leu
        290                 295                 300

Gly Gly Trp Leu Ser Asp Leu Ala Asn Ser Tyr Ala Glu Ile Lys Gly
305                 310                 315                 320

Arg Met Thr Val Gln Phe Thr Leu Val Leu Phe Glu Ser Ile Phe Ile
                325                 330                 335

Ile Trp Phe Ser His Ala Arg Thr Gln Thr Glu Ala Thr Leu Leu Leu
                340                 345                 350

Leu Ala Phe Ser Ile Phe Val Gln Ala Ala Asn Gly Ser Cys Phe Ala
                355                 360                 365

Ile Thr Pro Tyr Ile Ala Lys Ser Ala Gly Gly Ser Val Ser Gly Ile
        370                 375                 380

Val Gly Ala Gly Gly Asn Cys Gly Ala Val Ile Phe Thr Leu Leu Phe
385                 390                 395                 400

Leu His Gly Lys Phe Ser Ser Thr Ala Gln Gly Phe Arg Ile Met Gly
                405                 410                 415

Trp Cys Val Met Ala Val Ser Phe Thr Ile Trp Phe Leu Arg Pro Asp
                420                 425                 430

Leu Leu Ala Val Asp Pro Leu Ser Asp Thr Val Arg Ser Asp Ala Ser
        435                 440                 445

Val Glu Ala Ala Glu Glu Ala Asp Ala Val Glu Met Gly Asn Val Ala
        450                 455                 460

Lys Val Thr Ala
465

<210> SEQ ID NO 42
<211> LENGTH: 847
<212> TYPE: PRT
<213> ORGANISM: Nannochloropsis oculata

<400> SEQUENCE: 42

Met Thr His Pro Pro His Asn Glu Gly Arg Cys Arg Ser Ser Phe Ser
1               5                   10                  15

Thr Leu Leu Leu Tyr Met Ala Phe Lys Leu Ser Pro Gln Val Pro Thr
                20                  25                  30

Ala Pro Glu Pro Val Arg Ala Thr Ser Thr Asp Ala Arg Asp Asp Asp
        35                  40                  45
```

```
Thr Ala Asp Lys Trp Val Gln Arg Leu Pro Gly Met Ile Arg Leu Thr
    50                  55                  60

Gly Arg His Pro Phe Asn Ala Glu Pro His Thr Lys Glu Leu Val Asp
65                  70                  75                  80

Ala Gly Phe Ile Thr Pro Ala Ala Met His Tyr Val Arg Asn His Gly
                85                  90                  95

Pro Val Pro Lys Leu Ala Trp Asp Asp His Arg Ile Thr Val Thr Gly
                100                 105                 110

Leu Gly Val Ala Glu Pro Gln Val Leu Ser Met Asp Glu Leu Val Ala
            115                 120                 125

Leu Pro Asn Arg Thr Leu Pro Val Thr Leu Val Cys Ala Gly Asn Arg
        130                 135                 140

Arg Lys Glu Val Asn Val Thr Arg Gln Ser Lys Gly Phe Ser Trp Gly
145                 150                 155                 160

Ser Gly Ala Val Ser Thr Ser Ile Trp Thr Gly Val Pro Leu His Val
                165                 170                 175

Leu Leu Arg His Cys Gly Val Asp Pro Asp Ala Leu Glu Pro Gly Gln
            180                 185                 190

Tyr Trp Val Asn Phe Asp Gly Pro Asp Gly Glu Leu Pro Lys Gly Ile
            195                 200                 205

Tyr Gly Thr Ser Ile Pro Leu Leu Lys Ala Leu Asp Pro Ala Gln Asp
    210                 215                 220

Val Leu Val Ala Phe Lys Gln Asn His Glu Arg Leu Leu Pro Asp His
225                 230                 235                 240

Gly Phe Pro Val Arg Leu Ile Ile Pro Gly Tyr Ile Gly Gly Arg Met
                245                 250                 255

Ile Lys Trp Leu Thr Arg Ile Thr Ile Ser Arg Gln Glu Ser Gln Ser
            260                 265                 270

Phe Tyr His Phe His Asp Asn Arg Val Leu Pro Ser Ser Val Asp Gln
        275                 280                 285

Glu Arg Ala Asp Asn Glu Gly Trp Trp Arg Lys Pro Glu Tyr Ile Ile
    290                 295                 300

Asn Asp Leu Asn Leu Asn Ser Ala Ile Thr His Pro Thr His Asp Glu
305                 310                 315                 320

Glu Ile Pro Leu Lys Lys Gly Thr Tyr Lys Leu Gln Gly Tyr Ala Tyr
                325                 330                 335

Cys Gly Gly Gly Arg Gln Val Gln Arg Met Glu Val Ser Leu Asp Asp
            340                 345                 350

Gly Lys Ser Trp Glu Leu Ala Gln Leu Ser Ser Glu Glu Tyr Pro Thr
        355                 360                 365

Glu His Gly Arg Phe Trp Cys Trp Arg Ile Trp Asn Leu Asp Val Asp
    370                 375                 380

Ile Leu Arg Leu Val Gly Cys Thr Asn Val Ala Cys Arg Ala Trp Asp
385                 390                 395                 400

Asn Ser Gln Asn Thr Gln Pro Arg Asp Leu Thr Trp Asn Val Leu Gly
                405                 410                 415

Met Met Asn Asn Ser Trp Phe Arg Leu Thr Thr Ala Val Ser Leu Asn
            420                 425                 430

Asp Arg Gln Gln Pro Val Val Arg Ile Lys His Pro Ala Pro Ile Ala
        435                 440                 445

Pro Gly Gly Trp Met Glu Ala Gly Ala Asp Glu Thr Val Asn Val Gln
    450                 455                 460
```

-continued

```
Ala Lys Thr Thr Gly Thr Gly Ser Gly Arg Ser His Val Glu Asp Lys
465             470             475             480

Ser Val Pro Ser Ile Ala Gln Arg Lys Asp Leu Ser Val Ile Thr Arg
            485             490             495

Glu Glu Leu Ala Arg His Asn Ser Lys Thr Asp Cys Trp Ile Ala Val
            500             505             510

Lys Gly Gln Val Tyr Asp Val Thr Pro Tyr Leu Gln Glu His Pro Gly
            515             520             525

Gly Val Ala Ala Ile Val Met Asn Ala Gly Lys Asp Ala Thr Glu Asp
            530             535             540

Phe Glu Ala Ile His Ser Lys Arg Ala Trp Ala Met Leu Asp Glu Tyr
545             550             555             560

Leu Val Gly Thr Leu Gly Ala Ser Leu Thr Ser Ser Ser Pro Glu Ala
            565             570             575

Ser Ala Ile Ala Ala Pro Lys Glu Ala Ala Val Ala Leu Gln Gly Lys
            580             585             590

Asn Arg Ala Ile Lys Cys Lys Leu Val Phe Lys Glu Tyr Glu Ser Pro
            595             600             605

Asp Val Leu Arg Ile Arg Phe Gly Leu Pro Gln Pro Asp Gln Pro Leu
            610             615             620

Gly Leu Pro Val Gly Met His Ile Gly Leu Arg Ala Val Ile Asn Gly
625             630             635             640

Glu Ser Thr Lys Arg Gln Tyr Thr Pro Val Ser Asp Gly Asp Ala Lys
            645             650             655

Gly His Val Glu Leu Leu Val Lys Val Tyr Arg Ala Asn Gln His Pro
            660             665             670

Arg Phe Pro Asp Gly Gly Leu Met Ser Gln His Leu Asp Arg Met Ser
            675             680             685

Leu Gly Asp Cys Ile Asp Ile Asp Gly Pro Leu Gly His Ile Thr Tyr
            690             695             700

Glu Gly Pro Gly Cys Ile Arg Gln Leu Gly Glu Asp Val His Val Lys
705             710             715             720

His Phe Val Ala Val Ala Gly Gly Thr Gly Ile Thr Pro Val Val Gln
            725             730             735

Val Leu Arg Ala Val Leu Glu Asn Pro Cys Asp Thr Thr Arg Phe Ser
            740             745             750

Leu Ile Tyr Ala Ala Arg Val Pro Glu Asp Leu Leu Leu Arg Glu Glu
            755             760             765

Leu Asp Ala Trp Ala Glu Gln Tyr Glu Gln Phe Thr Val His Tyr Thr
            770             775             780

Val Asp Val Pro Pro Pro Asp Trp Pro Tyr Ser Val Gly Phe Leu Thr
785             790             795             800

Ala Glu Met Leu Ala Ala Asn Phe Pro Glu Ala Thr Lys Asp Met Gly
            805             810             815

Ala Leu Ile Cys Gly Pro Pro Pro Met Val Asn Phe Ala Val Lys Pro
            820             825             830

Asn Leu Glu Lys Leu Gly Tyr Thr Glu Asp Gln Phe Phe Ile Phe
            835             840             845
```